(12) United States Patent
Limem et al.

(10) Patent No.: US 11,903,815 B2
(45) Date of Patent: Feb. 20, 2024

(54) IMPLANTS ASSEMBLED FROM SKELETAL POLYHEDRON UNIT CELLS, COILED UNIT CELLS OR MESH UNIT CELLS

(71) Applicant: Tepha, Inc., Lexington, MA (US)

(72) Inventors: Skander Limem, Melrose, MA (US); Said Rizk, Windham, NH (US); Simon F. Williams, Cambridge, MA (US)

(73) Assignee: Tepha, Inc., Lexington, MA (US)

( * ) Notice: Subject to any disclaimer, the term of this patent is extended or adjusted under 35 U.S.C. 154(b) by 270 days.

(21) Appl. No.: 16/859,831

(22) Filed: Apr. 27, 2020

(65) Prior Publication Data

US 2020/0375726 A1 Dec. 3, 2020

Related U.S. Application Data

(60) Provisional application No. 62/855,835, filed on May 31, 2019.

(51) Int. Cl.
*A61F 2/12* (2006.01)
*A61F 2/00* (2006.01)
(Continued)

(52) U.S. Cl.
CPC .............. *A61F 2/12* (2013.01); *A61F 2/0063* (2013.01); *A61L 27/3687* (2013.01); *A61L 27/56* (2013.01); *A61L 27/58* (2013.01)

(58) Field of Classification Search
CPC .. A61F 2/12; A61F 2/0063; A61F 2210/0004; A61F 2210/00; A61L 27/3687;
(Continued)

(56) References Cited

U.S. PATENT DOCUMENTS 10,709,539 B2 7/2020 Mathisen et al.
10,722,336 B2 7/2020 Mathisen et al.
(Continued)

FOREIGN PATENT DOCUMENTS

WO 2015164982 A1 11/2015
WO 2016038083 A1 3/2016
(Continued)

OTHER PUBLICATIONS

PCTUS20200030141_ISR_Opinion_Dec. 3, 2020.
(Continued)

*Primary Examiner* — Brian A Dukert
*Assistant Examiner* — Rebecca Lynee Zimmerman
(74) *Attorney, Agent, or Firm* — Wolf, Greenfield & Sacks, P.C.

(57) ABSTRACT

Absorbable implants can be used to create volume and shape in soft tissues with regenerated tissue. The implants comprise lattices formed from multiple unit cells. Unit cells can be coils or springs, skeletal polyhedrons, foams, or structures derived from mesh and fiber. The implants may be coated or filled with cells and tissues, and preferably with autologous fat graft. The implants are particularly suitable for use in plastic surgery procedures, for example, to regenerate or augment breast tissue following mastectomy or in mastopexy procedures, and can provide an alternative to the use of permanent breast implants in these procedures.

24 Claims, 12 Drawing Sheets

(51) Int. Cl.
*A61L 27/36* (2006.01)
*A61L 27/56* (2006.01)
*A61L 27/58* (2006.01)

(58) Field of Classification Search
CPC .......... A61L 27/56; A61L 27/58; A61L 27/18; A61L 27/48; A61L 27/50; A61L 2430/04
See application file for complete search history.

(56) References Cited

U.S. PATENT DOCUMENTS

| | | |
|---|---|---|
| 2014/0222161 A1 | 8/2014 | Mathisen |
| 2018/0206978 A1 | 7/2018 | Rehnke |
| 2018/0280145 A1 | 10/2018 | Jones et al. |
| 2019/0247180 A1 | 8/2019 | Limem et al. |
| 2020/0107921 A1 | 4/2020 | Mathisen et al. |
| 2020/0179570 A1* | 6/2020 | Heschel ................ A61F 2/28 |
| 2020/0261202 A1* | 8/2020 | Mathisen .............. A61L 27/225 |
| 2020/0375715 A1 | 12/2020 | Egnelöv |
| 2021/0369912 A1* | 12/2021 | Toro Estrella ......... C12M 25/14 |

FOREIGN PATENT DOCUMENTS

| | | |
|---|---|---|
| WO | 2017050837 A1 | 3/2017 |
| WO | 2018078489 A1 | 5/2018 |
| WO | 2018177856 A1 | 10/2018 |
| WO | 2019217335 A1 | 11/2019 |

OTHER PUBLICATIONS

International Preliminary Report on Patentability dated Dec. 9, 2021 in connection with International Application No. PCT/US2020/030141.
PCT/US2020/030141, Dec. 9, 2021, International Preliminary Report on Patentability.
Muran Zhou et al, Tuning the mechanics of 3D-printed scaffolds by crystal lattice-like structural design for breast tissue engineering, 2020 Biofabrication 12 015023.

* cited by examiner

IMPLANTS ASSEMBLED FROM SKELETAL POLYHEDRON UNIT CELLS, COILED UNIT CELLS OR MESH UNIT CELLS

CROSS-REFERENCE TO RELATED APPLICATIONS

This application claims the benefit of U.S. Provisional Application No. 62/855,835, filed May 31, 2019, entitled "IMPLANTS ASSEMBLED FROM SKELETAL POLYHEDRON UNIT CELLS, COILED UNIT CELLS OR MESH UNIT CELLS", the entire contents of which are incorporated herein by reference in their entirety for all purposes.

FIELD OF THE INVENTION

The present invention generally relates to implants and more particularly to absorbable implants formed of three-dimensional unit cells.

BACKGROUND OF THE INVENTION

Breast reconstruction following mastectomy has become an integral and important part of breast cancer treatment with the surgery providing the patient with both aesthetic and psychosocial benefits. In the US, nearly 65% of breast reconstruction procedures now use a tissue expander to create a pocket for a permanent breast implant in the first step of the procedure. In some patients, a pocket for the breast implant can be formed without the use of a tissue expander. Once a pocket has been created, the tissue expander is removed, and replaced with a permanent breast implant in a second step.

Breast implants can also be used in breast augmentation and mastopexy procedures to augment breast size. In the latter procedure, a breast lift is combined with breast augmentation. Most commonly, the breast implant is placed in a pocket under the breast tissue, but in some cases, it is implanted under the chest wall.

Breast implants differ in dimensions, shape, and surface texture. A wide variety of different dimensions are available allowing the surgeon and patient to select from a range of projections, heights, widths and overall volume. In terms of shape, there are round and anatomically shaped implants, and the surfaces of the implants may be smooth, micro-textured or macro-textured. Generally, round implants have smooth surfaces, whereas anatomically shaped implants have dimpled micro- or macro-textured surfaces.

A growing number of patients considering breast reconstruction and augmentation are however reluctant to have permanent breast implants placed in their breasts. This is particularly the case for women that have had a mastectomy, and are now considering breast reconstruction. Some of these patients do not want to have a permanent foreign body placed in their breasts, and don't want to run the risk of complications that can develop with permanent breast implants. The complications include a risk of: capsular contraction requiring reoperation, rupture or deflation of the implant, development of anaplastic large cell lymphoma (ALCL), infection, and movement of the implants causing asymmetry of the breasts.

WO2016/038083 to Hutmacher discloses implants comprising voids filled with space-occupying structures designed to prevent invasion of tissue or individual cells into the voids. Six to eight weeks after implantation, the implants are removed leaving void spaces that can be filled with transplantation cells. The void spaces provide a pre-formed bed of connective tissue and vasculature to support the transplantation cells. The implant scaffolding structure can be made of a biodegradable material.

US2018/0206978 to Rehnke discloses an internal brassiere device made from a pleated scaffold that can be used in breast augmentation patients.

WO2018/078489 to Danze discloses an implant for replacing or increasing the volume of soft tissue comprising a three-dimensional bioabsorbable frame with two lateral openings, comprising two sheets of a bioabsorbable textile stacked on each other inside the frame of the implant.

Notably, there is very little innovation in the design of breast implants that when implanted can generate new breast tissue with a specific and desirable appearance. Thus, there is still a need for a breast implant that can not only serve as a scaffold for tissue in-growth, but also an implant that is soft to touch, can be compressed, can recover from compression, and can regenerate tissue in the breast that restores the normal feeling of the breast. More specifically, there is still a need for an implant that can be used to form new breast tissue, that preferably also has an elastic modulus similar to breast tissue, and preferably has a similar feel to breast tissue.

SUMMARY OF THE INVENTION

Implants described herein assist the surgeon in reshaping parts of the body, including the breast, nipple, face, and buttocks, as well as filling voids, reconstructing lost or missing tissue, supporting a damaged tissue structure, enhancing an existing tissue structure, increasing soft tissue volume, restoring tissue or organ function, restoring the natural feeling of soft tissue, repairing hernias, and delivering biological and synthetic materials to assist in tissue regeneration, repair, reinforcement, and reconstruction.

In embodiments, absorbable implants comprise a framework or lattice formed from multiple unit cells. The unit cells can be skeletal polyhedrons with edges and vertices formed from polymeric struts or fibers, coils or springs, or unit cells formed from knitted mesh or foams.

In embodiments, the implants are porous, providing scaffolding for tissue ingrowth, and may further comprise cells, collagen, autologous fat, fat lipoaspirate, or injectable fat.

In embodiments, the implants are compressible, and recover their shape after compression.

In embodiments, the implant is used in soft tissue repair, regeneration, and replacement. Indeed, the implant described herein can be operable as any one type of device selected from a wide range of devices including, for example, a plastic surgery device, breast implant, breast lift device, breast augmentation device, nipple implant, facial reconstruction device, buttock implant, malar augmentation device, cosmetic repair device, soft tissue regeneration device, hernia implant, hernia plug, wound healing device, tissue engineering scaffold, scaffold to deliver a vascular pedicle, guided tissue repair/regeneration device, bulking or filling device, void filler, device for treatment of vesicoureteral reflux, cell seeded device, or a drug delivery device.

In embodiments, the polymeric struts or fibers of the unit cells forming the skeletal polyhedrons, or the coils or springs forming the unit cells of the skeletal polyhedrons have one or more of the following properties: (i) diameters of 0.025 to 3 mm, more preferably 0.1 to 2 mm, and even more preferably 0.15 to 1 mm; (ii) breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa.

In embodiments, an implant has solely one type of unit cells, wherein each unit cell is identical. Such implants may be formed from skeletal polyhedrons where all of these property values are the same within the skeletal polyhedron. In other embodiments, an implant has more than one type of unit cells. Such implants may be formed from skeletal polyhedrons where the polymeric struts and fibers, or coils and springs, have different property values.

In embodiments, the implants include resorbable polymeric struts or fibers.

In embodiments, the implant can be a scaffold for allograft or xenograft tissue and cells, but preferably for autologous tissue and cells, including, but not limited to, autologous fat, fat lipoaspirate, lipo-filling, injectable fat, adipose cells, fibroblast cells, and stem cells. In embodiments, the implant may be an adipose tissue engineering scaffold. In embodiments, the implant may comprise collagen. In embodiments, the implant may have one or more openings to allow insertion of a vascular pedicle or other tissue mass. The implants are designed to encourage tissue ingrowth. The implants are designed for use in repairing, replacing, regenerating and augmenting soft tissue structures. Following implantation, the implant is designed to be invaded by connective tissue and bloods vessels, and become well integrated. Preferably, the implants are porous, absorbable, degrade in a controlled manner, and are replaced in vivo by the patient's tissue. The implants may be macro-porous. The implants preferably comprise a polymeric material with a predictable rate of degradation, and a predictable strength retention in vivo. The implants can allow tissue mass to be restored or augmented with restoration or maintenance of the tactile sensation of tissue, which is particularly important for applications involving the breast, nipple, face, neck, buttocks and skin.

In embodiments, the implants contain lattices formed from multiple unit cells. Unit cells may be repeated to form the volume of the implant, and, if desired, the surface of the unit cells may be trimmed to form the final shape of the implant. The repeating unit cells of the implants make it possible to produce implants with predictable properties. The implants are preferably 3-dimensional in shape. In embodiments, the unit cells are skeletal polyhedrons with edges and vertices formed from polymeric struts or fibers. In other embodiments, the unit cells are coils or springs formed from polymers. In yet other embodiments, the unit cells are knitted mesh formed from polymers. In yet further embodiments, the unit cells are foams formed from polymers. The unit cells are hollow or porous such that the lattices are space-occupying structures. In embodiments, a unit cell of the lattice is joined to one or more different unit cells. A lattice may comprise two or more unit cells, and preferably 50 or more unit cells. The unit cells of the lattices are preferably colonized by cells prior to implantation or, more preferably, following implantation, and the pores of the lattices can be invaded by tissue, blood vessels or a combination thereof. When the lattices are absorbable, degradation of the lattice can allow further invasion of the lattice structure with tissue, blood vessels or a combination thereof, and this process can continue until the lattice is completely absorbed. In embodiments, the lattices may comprise one or more openings to allow, for example, insertion of a vascular pedicle or other tissue mass. In embodiments, the one or more openings may form a transverse passage within the lattice.

In embodiments, the implants can have anisotropic properties meaning that the implants have different properties in different directions. The implants may have a first elastic modulus in one direction, and a second different elastic modulus in a second direction. The implants may have high strength relative to their volumetric density.

In embodiments, the implants are soft tissue implants comprising a porous lattice, wherein the lattice further comprises connected unit cells, and wherein the unit cells are skeletal polyhedrons, and the edges and vertices of the skeletal polyhedrons are formed from polymeric struts or fibers. In embodiments, the implants are soft tissue implants comprising a porous lattice, wherein the lattice further comprises connected unit cells, and wherein the unit cells are coils or springs, and the coils or springs are formed from polymeric struts or fibers. In yet other embodiments, the implants are soft tissue implants comprising a porous lattice, wherein the lattice further comprises connected unit cells, and wherein the unit cells are knitted, with top and bottom plates of knitted mesh connected by fiber, preferably wherein the unit cells are warp knitted. In embodiments, the unit cells are foams, preferably compressible foams.

In embodiments, the implant is a plastic surgery device, breast implant, breast lift device, breast augmentation device, nipple implant, facial reconstruction device, buttock implant, malar augmentation device, cosmetic repair device, soft tissue regeneration device, hernia implant, hernia plug, wound healing device, tissue engineering scaffold, scaffold for a vascular pedicle or other tissue mass, guided tissue repair/regeneration device, bulking or filling device, void filler, device for treatment of vesicoureteral reflux, cell seeded device, or a drug delivery device.

In a preferred embodiment, the implant is an absorbable breast implant, and optionally is coated with autologous tissue from the patient prior to implantation, during implantation, or after implantation, or any combination thereof. The autologous tissue is preferably one or more of the following: autologous fat, fat lipoaspirate, injectable fat, adipose cells, fibroblast cells, and stem cells. The breast implant is preferably macro-porous. The breast implant's macro-porosity is designed to allow the implant to accommodate sufficient autologous fat, biological materials, collagen, hyaluronic acid and or bioactive agents, in order to facilitate vascularization and tissue in-growth within the implant of a relatively large volume of breast tissue. Optionally, the breast implant may further comprise one or more openings, including a transverse passage to allow insertion of a vascular pedicle or other tissue mass. The implant can be used in patients that have: (i) undergone mastectomy, (ii) undergone breast lift and have need of an augmentation, (iii) undergone breast reduction and need support and lift of the reduced breast, (iv) undergone prior silicone breast implant breast surgery, and desire that the silicone implant is removed and that there is subsequent reconstruction of the breast to produce a youthful appearance but with a fuller breast and larger size. The implant may also be used in patients that want the feeling of natural breast tissue restored to the breast after removal of their breast tissue. The implant can be used to increase projection of the breast from the chest, and in combination with fat grafting to add volume to the breast.

In embodiments, the implant is a breast lift device, breast augmentation device, or a replacement or substitute for a permanent breast implant. In embodiments, the implant has a shape and size suitable for use in breast surgery procedures, including breast augmentation, breast reconstruction and mastopexy.

In embodiments, the implant is a breast implant, and even more preferably can be compressed and recover from compression. In embodiments, an implant is engineered with a shape that produces a specific and desirable appearance of the breast. Ideally, the breast implant has a similar elastic modulus to breast tissue. In embodiments, the implanted breast implant has a similar feel to breast tissue. After implantation of the breast implant, the breast does not feel hard, but rather is soft to touch and feels like a natural breast. Furthermore, in embodiments, the breast implant allows restoration of breast mass or augmentation of breast mass while maintaining tactile sensation or restoring tactile sensation.

In embodiments, the implant retains strength long enough to allow support at the implant site to be transitioned from the implant to new tissue. The implant needs to maintain its shape for a prolonged period in order to direct re-modeling of the patient's tissue. When the implant is used as a breast implant, the implant provides support of the breast until support is transitioned from the implant to new tissue. Preferably, no loss of support, or minimal loss of support, for the breast tissue occurs during this transition period. The shape of the breast implant is maintained for a prolonged period in order to direct tissue in-growth into the implant, and produce the desired breast shape.

In embodiments, the implant has a pre-determined three-dimensional shape. In the case of a breast implant, the implant has a pre-determined three-dimensional shape that can be implanted subcutaneously, between the skin and the breast mound or chest wall of the breast. The breast implant may be implanted in the pre-pectoral, sub-glandular or sub-pectoral positions. The implant allows the surgeon to easily control the volumetric ratios of the upper and lower poles of the breast, the extent of protrusion of the breast from the chest wall, and the curvatures of the upper and lower poles of the breast. The surgeon may insert a vascular pedicle or other tissue mass into the implant prior to implantation.

In embodiments, the implant serves to provide the surgeon with a means to deliver cells, stem cells, differentiated cells, fat cells, muscle cells, platelets, pedicles, vascular pedicles, tissue masses, extracellular adipose matrix proteins, gels, hydrogels, hyaluronic acid, collagen, bioactive agents, drugs, antibiotics, and other materials to the implant site. Preferably, the cells and tissues delivered by the implants, or coated or injected into the implants, are autologous. The implants may be used for autologous fat transfer. The cells added, coated or injected on the implant may include pancreatic islet cells, hepatic cells, and stem cells genetically altered to contain genes for treatment of patient illnesses. The implants may comprise bioactive agents to stimulate cell in-growth, including growth factors, cell adhesion factors, cellular differentiating factors, cellular recruiting factors, cell receptors, cell-binding factors, cell signaling molecules, such as cytokines, and molecules to promote cell migration, cell division, cell proliferation and extracellular matrix deposition. The implants may also be coated or contain agents to prevent tissue adhesion, or agents to prevent cell proliferation, particularly to delay cell invasion into the implant structure. Such agents may be present on or in all the lattice or just one or more specific area of the lattice.

In embodiments, the implants can be implanted to replace and or increase a soft tissue volume or a tissue mass. In embodiments, the implants may further comprise a growth chamber for cells and tissues. In embodiments, the implants may comprise one, two or more openings to allow the insertion of a vascular pedicle, or other mass of tissue into the implant or so that the implant sandwiches the vascular pedicle or other mass of tissue.

In embodiments, the implants have elastic modulus values from 0.01 kPa to 290 MPa, more preferably from 0.1 kPa to 10 MPa, and even more preferably from 0.1 kPa to 1 MPa or 0.1 kPa to 100 kPa. When the implant is a breast implant, the elastic modulus is preferably 0.01 kPa to 1 MPa, and more preferably 0.1 kPa to 100 kPa.

In embodiments, the implants can be temporarily deformed for implantation, for example, to allow minimally invasive delivery procedures. The lattice of the implant may be filled by injection with one or more of the following after implantation: cells, tissue and or lipoaspirate. A vascular pedicle or other tissue mass may be inserted prior to, or after the lattice has been filled with cells, tissue and or lipoaspirate.

In embodiments, the implants can be made from poly-4-hydroxybutyrate (P4HB) and copolymers thereof, or from poly(butylene succinate) (PBS) and copolymers thereof. The PBS polymer and copolymers may further comprise one or more of the following: branching agent, cross-linking agent, chain extender agent, and reactive blending agent. The PBS and P4HB polymers and copolymers may be isotopically enriched. In preferred embodiments, the lattice unit cells of the implants can be made from P4HB, PBS or copolymers of P4HB and PBS, by injection molding, extrusion, knitting, weaving, foaming, or 3D printing. In embodiments, the lattice is made of a material that can hold micro-globules of lipo-suctioned fat in place, and prevent pooling of fat which can lead to necrosis.

In embodiments, the polymers used to prepare the implants have weight average molecular weights of 50 to 1,000 kDa, more preferably 90 to 600 kDa, and even more preferably from 200 to 450 kDa.

In embodiments, the implants have an endotoxin content of less than 20 endotoxin units per implant. In embodiments, the implants have been sterilized by ethylene oxide, electron beam, or gamma-irradiation.

In embodiments, the implants are manufactured by forming a plurality of a first type of unit cell into a lattice, wherein (i) the unit cells are formed by injection molding a polymeric composition to form the struts or fibers of the unit cells, and the unit cells are assembled to form a lattice, (ii) the unit cells are formed by warp knitting of fiber, and the unit cells are assembled to form a lattice, (iii) the lattice is formed directly from a polymeric composition by 3D printing of the polymeric struts or fibers of the lattice, or (iv) the unit cells are formed by foaming, and the foam unit cells are assembled to form a lattice. The lattices so formed may: (i) have an elastic modulus of 0.01 kPa to 1 MPa, (ii) be trimmed after molding or printing, and or (iii) comprise one or more tabs or anchors for fixation of the implant. The lattices so formed by injection molding may further comprise fasteners that allow the unit cells to be attached to each other to form the lattice.

In embodiments, the implants may be temporarily deformed during implantation, or delivered by a minimally invasive technique.

In embodiments, the unit cells of the implants are formed with surface roughness (Ra). Surface roughness promotes cell attachment and tissue formation on the implants. Surface roughness also promotes attachment of the implant to neighboring tissues, encourages tissue in-growth, and helps to prevent movement of the device after implantation. In embodiments, the struts or fibers of the implant's unit cells have a surface roughness of 0.02 to 75 microns, more preferably 0.1 to 50 or 0.5 to 30 microns, and even more preferably 5 to 30 microns. In embodiments, the unit cells of the implants are 3D printed with these surface roughness values. Preferably, the unit cells of the implants are 3D printed by Selective Laser Melting (SLM) of polymer powder or Melt Extrusion Deposition (MED) of polymer pellets. In embodiments, the unit cells are formed from extruded fibers with surface roughness. In embodiments, extruded fibers with surface roughness may be formed by inducing melt fracture during fiber extrusion, using textured nip rollers to form roughness on the fiber surface after extrusion, extruding fiber through a featured die hole, for example, a serrated hole, and treating extruded fiber with a solvent vapor mist that creates divots on the fiber surface, for example, using micron sized droplets of solvent. In embodiments, the implants are formed from unit cells comprising struts or fibers with surface roughness of 0.02 to 75 microns, more preferably 0.1 to 50 microns, and the struts or fibers have one or more of the following properties: (i) diameters of 0.025 to 3 mm, more preferably 0.1 to 2 mm, and even more preferably 0.15 to 1 mm; (ii) breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa. In embodiments, the implants are formed from unit cells comprising struts or fibers with surface roughness of 0.02 to 75 microns, more preferably 0.1 to 50 microns, and the implants have an elastic modulus of 0.01 kPa to 290 MPa, more preferably from 0.1 kPa to 10 MPa. In embodiments, the implants with surface roughness are breast implants.

In embodiments, the implants are not permanent, and degrade with a predictable rate and have a predictable strength retention that allows support to be transitioned from the implant to new tissue.

In embodiments, the implants have a scaffolding structure that can be coated with, or act as a reservoir for, autologous tissue, including, but not limited to, autologous fat, fat lipoaspirate, injectable fat, adipose cells, fibroblast cells, and stem cells.

In embodiments, the implants comprise one or more openings to allow insertion of a vascular pedicle or other tissue mass in order to increase or replace tissue volume.

In embodiments, the implants can be easily engineered into any shape, for example, shapes that provide a specific and desirable appearance of the breast.

These advantages as well as other objects and advantages of the present invention will become apparent from the detailed description to follow, together with the accompanying drawings.

DETAILED DESCRIPTION OF THE INVENTION

Figure 1:
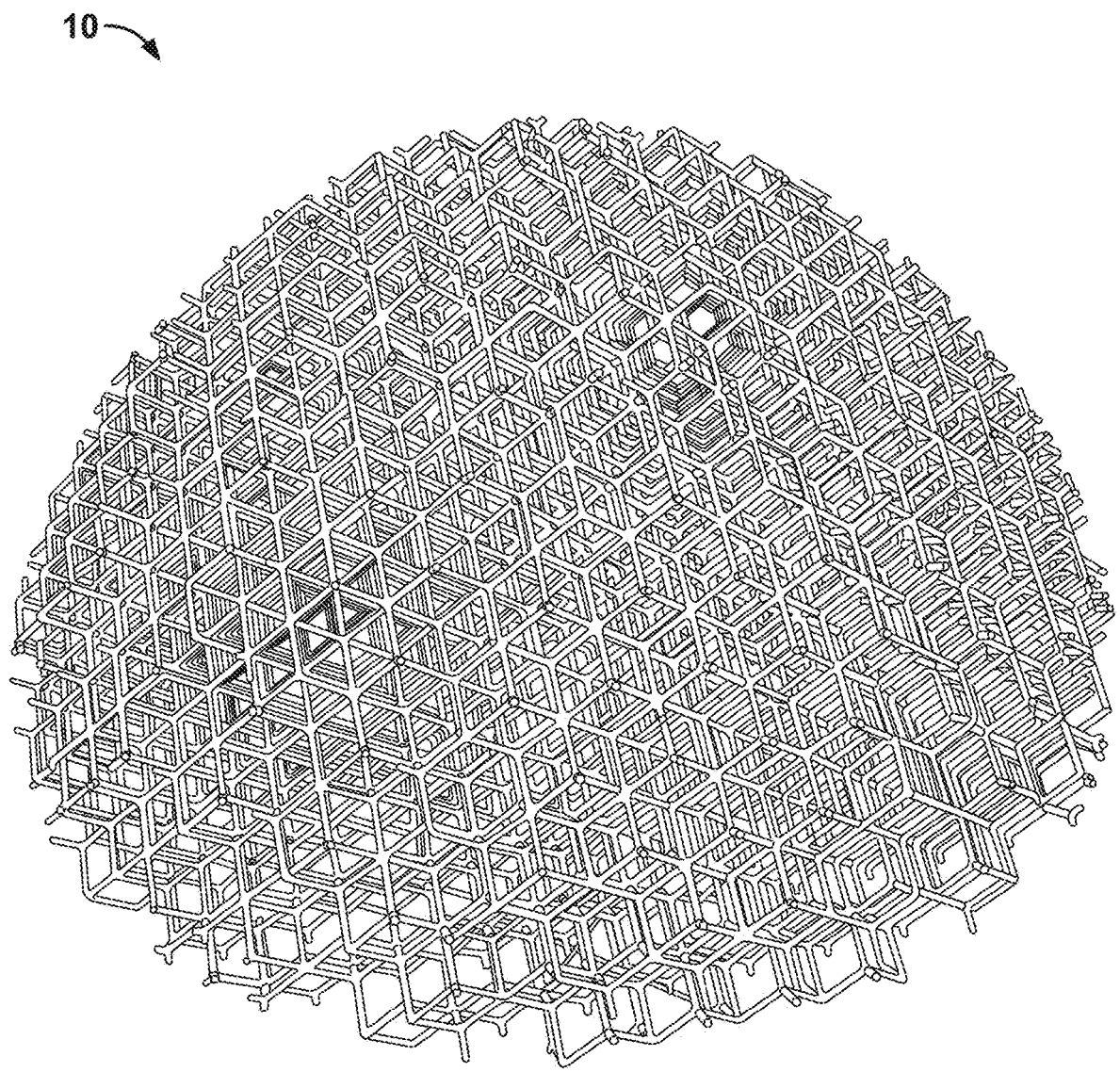
FIG. 1 is a perspective view of an implant including a plurality of connected skeletal polyhedron unit cells in accordance with an embodiment of the invention.
Figure 2A:
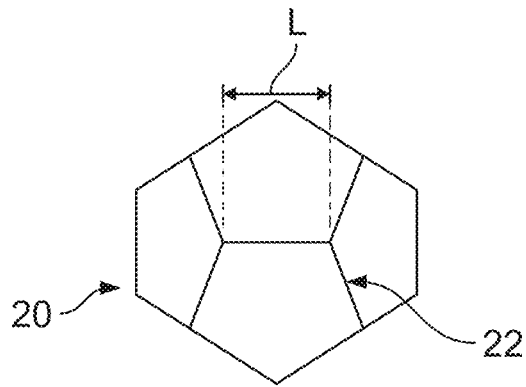
FIGS. 2A-2D are respectively a bottom view, isometric view, front view and left view of one skeletal polyhedron unit cell of the implant shown in FIG. 1.
Figure 2B:
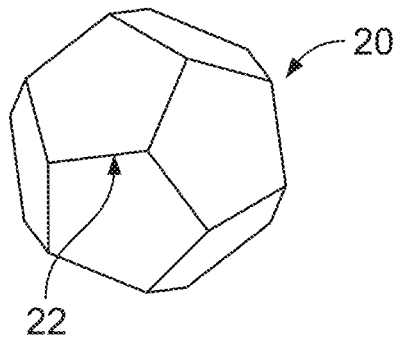
Figure 2C:
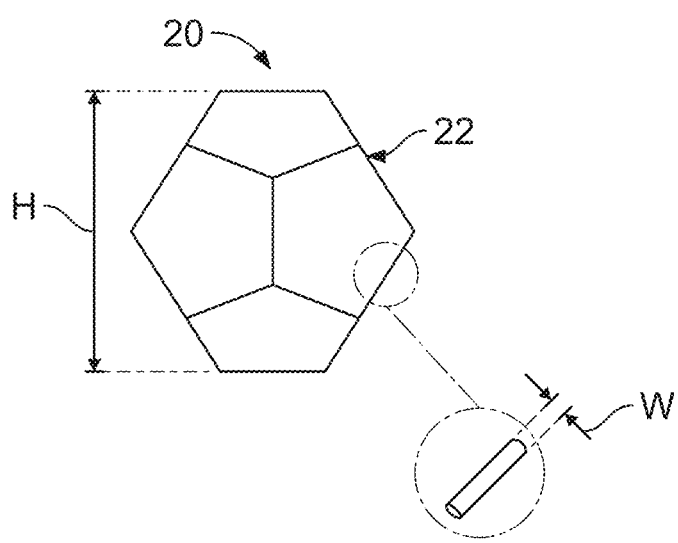
Figure 2D:
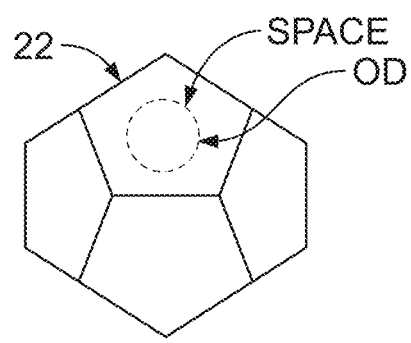

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

To further assist in understanding the following definitions are set forth below. However, it is also to be appreciated that unless defined otherwise as described herein, all technical and scientific terms used herein have the same meaning as commonly understood by one of ordinary skill in the art to which this invention belongs.

I. Definitions

"Absorbable" as generally used herein means the material is degraded in the body, and the degradation products are eliminated or excreted from the body. The terms "absorbable", "resorbable", "degradable", and "erodible", with or without the prefix "bio", can be used interchangeably herein, to describe materials broken down and gradually absorbed, excreted, or eliminated by the body, whether degradation is due mainly to hydrolysis or mediated by metabolic processes.

"Bioactive agent" as generally used herein refers to therapeutic, prophylactic or diagnostic agents, preferably agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Copolymers of poly-4-hydroxybutyrate" as generally used herein means any polymer containing 4-hydroxybutyrate with one or more different hydroxy acid units. The copolymers may be isotopically enriched.

"Copolymers of poly(butylene succinate)" as generally used herein means any polymer containing 1,4-butanediol and succinic acid units, and one or more different diol or diacid units. The copolymers may include one or more of the following: branching agent, cross-linking agent, chain extender agent, and reactive blending agent. The copolymers may be isotopically enriched.

"Endotoxin content" as generally used herein refers to the amount of endotoxin present in an implant or sample, and is determined by the limulus amebocyte lysate (LAL) assay.

"Molecular weight" as generally used herein, unless otherwise specified, refers to the weight average molecular weight (Mw), not the number average molecular weight (Mn), and is measured by GPC relative to polystyrene.

"Pitch" as generally used herein to describe a coil or spring means the distance between the wires of adjacent coils, and is measured from the center of a wire to the center of an adjacent wire.

"Poly(butylene succinate) mean a polymer containing 1,4-butanediol units and succinic acid units. The polymer may include one or more of the following: branching agent, cross-linking agent, chain extender agent, and reactive blending agent. The polymer may be isotopically enriched.

"Poly(butylene succinate) and copolymers" includes polymers and copolymers prepared with one or more of the following: chain extenders, coupling agents, cross-linking agents and branching agents.

"Poly-4-hydroxybutyrate" as generally used herein means a homopolymer containing 4-hydroxybutyrate units. It can be referred to herein as P4HB or TephaFLEX® biomaterial (manufactured by Tepha, Inc., Lexington, MA). The polymers may be isotopically enriched.

"Pre-pectoral" as used herein means under the skin and over or above the pectoral muscle.

"Skeleton polyhedron" as used herein means the perimeter framework consisting of the edges and vertices of a polyhedron and its interior is hollow, unless filled.

"Soft tissue" as used herein means body tissue that is not hardened or calcified. Soft tissue excludes hard tissues such as bone and tooth enamel.

"Strength retention" refers to the amount of time that a material maintains a particular mechanical property following implantation into a human or animal. For example, if the tensile strength of a resorbable fiber or strut decreases by half over 3 months when implanted into an animal, the fiber or strut's strength retention at 3 months would be 50%.

"Sub-glandular" as used herein means under the breast tissue and above the pectoral muscle.

"Sub-pectoral" as used herein means at least partially under the pectoral muscle.

"Surface roughness" (Ra) as used herein is the arithmetic average of the absolute values of the profile height deviations from a mean line, recorded within an evaluation length.

"Volumetric density" as used herein means the ratio of the volume of the material forming the unit cells of the implant's lattice divided by the volume of the voids in the implant's lattice. For example, an implant with a volumetric density of 20% would have a lattice containing 20% material by volume and 80% voids by volume. The volumetric density is measured prior to applying any additives, bioactive agents, cells and tissue to the lattice.

II. Materials for Preparing Implants

In embodiments, the implants can be used to reshape parts of the body, including the breast, nipple, face, and buttocks, as well as fill voids, repair hernias, and deliver biological and synthetic materials to assist in tissue regeneration, augmentation, repair, reinforcement, and reconstruction. The implants are soft tissue implants meaning that they can be used for soft tissue regeneration, augmentation, repair, reinforcement, and reconstruction. The implants can eliminate the need to use permanent breast implants during mastectomy, mastopexy and breast augmentation procedures, as well as permanent implants in other surgical procedures. The implants are biocompatible, and are preferably replaced in vivo by the patient's tissue as the implants degrade. The implants are particularly suitable for filling voids or augmenting tissues, especially soft tissues. The implants can have a range of properties from stiff, rigid structures to structures that are soft and temporarily deform when a force is applied. The properties may be engineered to be similar to soft tissues. Implants made for the breast may be compressed, and can recover their shape following compression. Optionally, the implants can be coated with autologous tissue, autologous fat, fat lipoaspirate, injectable fat, adipose cells, fibroblast cells, and stem cells prior to implantation, during implantation, or post-implantation. The implants may further comprise one or more openings or passages, including a transverse passage, to allow insertion of a vascular pedicle or other tissue mass.

A. Polymers for Preparing Implants

In embodiments, the implants contain lattices that are formed from multiple unit cells. The shapes or types of the unit cells may vary. The shapes of the unit cells may be skeletal polyhedrons with edges and vertices formed from polymeric struts or fibers. Alternatively, the unit cells may be coils or springs formed from polymers. A third type of unit cell is the mesh unit cell wherein the top and bottom of the unit cell are formed from mesh, and the top and bottom meshes are connected together with struts or fiber to form the unit cell. A fourth type of unit cell is the foam unit cell, preferably a porous compressible unit cell. The implant's lattice structure is formed by joining together two or more unit cells. The unit cells that are joined together may be the same or different. A lattice may comprise 2 or more unit cells, and preferably 50 or more unit cells. The lattices may optionally comprise other features, such as one or more openings, or one or more passages, including one or more transverse passages.

The lattice of the implant may comprise permanent materials, such as non-degradable thermoplastic polymers, including polymers and copolymers of ethylene and propylene, including ultra-high molecular weight polyethylene, ultra-high molecular weight polypropylene, nylon, polyesters such as poly(ethylene terephthalate), poly(tetrafluoroethylene), polyurethanes, poly(ether-urethanes), poly(methylmethacrylate), polyether ether ketone, polyolefins, and poly(ethylene oxide). However, the lattice of the implant preferably comprises degradable materials, more preferably thermoplastic or polymeric degradable materials, and even more preferably the implant's lattice is made completely from degradable materials.

In a preferred embodiment, the implant's lattice is made from one or more absorbable polymers or copolymers, preferably absorbable thermoplastic polymers and copolymers, and even more preferably absorbable thermoplastic polyesters. The implant's lattice may, for example, be prepared from polymers including, but not limited to, polymers of glycolic acid, lactic acid, 1,4-dioxanone, trimethylene carbonate, 3-hydroxybutyric acid, 4-hydroxybutyrate, ε-caprolactone, including polyglycolic acid, polylactic acid, polydioxanone, polycaprolactone, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); polyhydroxyalkanoates; synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk (including recombinant silks and silk derivatives and analogs); chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolactone and copolymers thereof, including random copolymers and block copolymers thereof.

Preferably the lattice of the implant is prepared from an absorbable polymer or copolymer that will be substantially resorbed after implantation within a 1 to 24-month timeframe, more preferably 3 to 18-month timeframe, and retain some residual strength for at least 2 weeks to 6 months.

Blends of polymers and copolymers, preferably absorbable polymers, can also be used to prepare the implant's lattice. Particularly preferred blends of absorbable polymers are prepared from absorbable polymers including, but not limited to, polymers of glycolic acid, lactic acid, 1,4-dioxanone, trimethylene carbonate, 3-hydroxybutyric acid, 4-hydroxybutyrate, ε-caprolactone, 1,4-butanediol, 1,3-propane diol, ethylene glycol, glutaric acid, malonic acid, oxalic acid, succinic aid, adipic acid, or copolymers thereof.

In a particularly preferred embodiment, poly-4-hydroxybutyrate (Tepha's P4HB™ polymer, Lexington, MA) or a copolymer thereof is used to make the implant's lattice. Copolymers include P4HB with another hydroxyacid, such as 3-hydroxybutyrate, and P4HB with glycolic acid or lactic acid monomer. Poly-4-hydroxybutyrate is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene), more preferably from 100 kDa to 600 kDa, and even more preferably 200 kDa to 450 kDa. A weight average molecular weight of the polymer of 50 kDa or higher is preferred for processing and mechanical properties.

In another preferred embodiment, the lattice of the implant is prepared from a polymer comprising at least a diol and a diacid. In a particularly preferred embodiment, the polymer used to prepare the lattice is poly(butylene succinate) (PBS) wherein the diol is 1,4-butanediol and the diacid is succinic acid. The poly(butylene succinate) polymer may be a copolymer with other diols, other diacids or a combination thereof. For example, the polymer may be a poly(butylene succinate) copolymer that further comprises one or more of the following: 1,3-propanediol, ethylene glycol, 1,5-pentanediol, glutaric acid, adipic acid, terephthalic acid, malonic acid, methylsuccinic acid, dimethylsuccinic acid, and oxalic acid. Examples of preferred copolymers are: poly(butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate). The poly(butylene succinate) polymer or copolymer may also further comprise one or more of the following: chain extender, coupling agent, cross-linking agent and branching agent. For example, poly(butylene succinate) or copolymer thereof may be branched or cross-linked by adding one or more of the following agents: malic acid, trimethylol propane, trimesic acid, citric acid, glycerol propoxylate, and tartaric acid. Particularly preferred agents for branching or crosslinking the poly(butylene succinate) polymer or copolymer thereof are hydroxycarboxylic acid units. Preferably the hydroxycarboxylic acid unit has two carboxylic groups and one hydroxyl group, two hydroxyl groups and one carboxyl group, three carboxyl groups and one hydroxyl group, or two hydroxyl groups and two carboxyl groups. In one preferred embodiment, the implant's lattice is prepared from poly(butylene succinate) comprising malic acid as a branching or cross-linking agent. This polymer may be referred to as poly(butylene succinate) cross-linked with malic acid, succinic acid-1,4-butanediol-malic acid copolyester, or poly(1,4-butylene glycol-co-succinic acid), cross-linked with malic acid. It should be understood that references to malic acid and other cross-linking agents, coupling agents, branching agents and chain extenders include polymers prepared with these agents wherein the agent has undergone further reaction during processing. For example, the agent may undergo dehydration during polymerization. Thus, poly(butylene succinate)-malic acid copolymer refers to a copolymer prepared from succinic acid, 1,4-butanediol and malic acid. In another preferred embodiment, malic acid may be used as a branching or cross-linking agent to prepare a copolymer of poly(butylene succinate) with adipate, which may be referred to as poly[(butylene succinate)-co-adipate] cross-linked with malic acid. As used herein, "poly(butylene succinate) and copolymers" includes polymers and copolymers prepared with one or more of the following: chain extenders, coupling agents, cross-linking agents and branching agents. In a particularly preferred embodiment, the poly(butylene succinate) and copolymers thereof contain at least 70%, more preferably 80%, and even more preferably 90% by weight of succinic acid and 1,4-butanediol units. The polymers comprising diacid and diols, including poly (butylene succinate) and copolymers thereof and others described herein, preferably have a weight average molecular weight (Mw) of 10,000 to 400,000, more preferably 50,000 to 300,000 and even more preferably 100,000 to 200,000 based on gel permeation chromatography (GPC) relative to polystyrene standards. In a particularly preferred embodiment, the polymers and copolymers have a weight average molecular weight of 50,000 to 300,000, and more preferably 75,000 to 300,000. In one preferred embodiment, the poly(butylene succinate) or copolymer thereof used to make the lattice has one or more, or all of the following properties: density of 1.23-1.26 g/cm$^3$, glass transition temperature of −31° C. to −35° C., melting point of 113° C. to 117° C., melt flow rate (MFR) at 190° C./2.16 kgf of 2 to 10 g/10 min, and tensile strength of 30 to 60 MPa.

In another embodiment, the polymers and copolymers described herein that are used to prepare the lattice of the implant, including P4HB and copolymers thereof and PBS and copolymers thereof, include polymers and copolymers in which known isotopes of hydrogen, carbon and/or oxygen are enriched. Hydrogen has three naturally occurring isotopes, which include $^1$H (protium), $^2$H (deuterium) and $^3$H (tritium), the most common of which is the $^1$H isotope. The isotopic content of the polymer or copolymer can be enriched for example, so that the polymer or copolymer contains a higher than natural ratio of a specific isotope or isotopes. The carbon and oxygen content of the polymer or copolymer can also be enriched to contain higher than natural ratios of isotopes of carbon and oxygen, including, but not limited to $^{13}$C, $^{14}$C, $^{17}$O or $^{18}$O. Other isotopes of carbon, hydrogen and oxygen are known to one of ordinary skill in the art. A preferred hydrogen isotope enriched in P4HB or copolymer thereof or PBS or copolymer thereof is deuterium, i.e. deuterated P4HB or copolymer thereof or deuterated PBS or copolymer thereof. The percent deuteration can be up to at least 1% and up to 5, 10, 15, 20, 25, 30, 35, 40, 45, 50, 55, 60, 65, 70, 75, 80 or 85% or greater.

In a preferred embodiment, the polymers and copolymers that are used to prepare the lattice, including P4HB and copolymers thereof and PBS and copolymers thereof, have low moisture contents. This is preferable to ensure the implants can be produced with high tensile strength, prolonged strength retention, and good shelf life. In a preferred embodiment, the polymers and copolymers that are used to prepare the implants have a moisture content of less than 1,000 ppm (0.1 wt %), less than 500 ppm (0.05 wt %), less than 300 ppm (0.03 wt %), more preferably less than 100 ppm (0.01 wt %), and even more preferably less than 50 ppm (0.005 wt %).

The compositions used to prepare the implants desirably have a low endotoxin content. In preferred embodiments, the endotoxin content is low enough so that the implants produced from the polymer compositions have an endotoxin content of less than 20 endotoxin units per device as determined by the limulus amebocyte lysate (LAL) assay. In one embodiment, the polymeric compositions used to prepare the lattice of the implant have an endotoxin content of <2.5 EU/g of polymer or copolymer. For example, the P4HB polymer or copolymer, or PBS polymer of copolymer have an endotoxin content of <2.5 EU/g of polymer or copolymer.

B. Additives

Certain additives may be incorporated into the implant, preferably in the polymeric compositions that are used to make the lattice. In one embodiment, these additives are incorporated with the polymers or copolymers described herein during a compounding process to produce pellets that can be subsequently processed to produce the lattices. For example, pellets may be injection molded, extruded or printed to form lattices or unit cells of the lattices. In another embodiment, the pellets may be ground to produce powders suitable for further processing, for example, by 3D printing. Or, powders suitable for further processing, for example by 3D printing, may be formed directly by blending the additives and polymer or copolymer. If necessary, powders used for processing may be sieved to select an optimum particle size range. In another embodiment, the additives may be incorporated into the polymeric compositions used to prepare the lattices of the implants using a solution-based process.

In a preferred embodiment, the additives are biocompatible, and even more preferably the additives are both biocompatible and resorbable.

In one embodiment, the additives may be nucleating agents and/or plasticizers. These additives may be added to the polymeric compositions used to prepare the lattices of the implants in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the lattice, and to improve the mechanical properties of the lattice. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the polymeric compositions for preparing the lattices of the implants include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Bioactive Agents, Cells and Tissues

The implants can be loaded, filled, coated, or otherwise incorporated with bioactive agents. Bioactive agents may be included in the implants for a variety of reasons. For example, bioactive agents may be included in order to improve tissue in-growth into the implant, to improve tissue maturation, to provide for the delivery of an active agent, to improve wettability of the implant, to prevent infection, and to improve cell attachment. The bioactive agents may also be incorporated into the lattice structure of the implant.

The implants can contain active agents designed to stimulate cell in-growth, including growth factors, cell adhesion factors including cell adhesion polypeptides, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The implants can incorporate wetting agents designed to improve the wettability of the surfaces of the lattice structures to allow fluids to be easily adsorbed onto the implant surfaces, and to promote cell attachment and or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The implants can contain gels, hydrogels or living hydrogel hybrids to further improve wetting properties and to promote cellular growth throughout the lattice structures of the implants. Hydrogel hybrids consist of living cells encapsulated in a biocompatible hydrogel like gelatin, methacrylated gelatin (GelMa), silk gels, and hyaluronic acid (HA) gels.

Other bioactive agents that can be incorporated in the implants include antimicrobial agents, in particular antibiotics, disinfectants, oncological agents, anti-scarring agents, anti-inflammatory agents, anesthetics, small molecule drugs, anti-adhesion agents, inhibitors of cell proliferation, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as hydroxyapatite and ceramics, or complex mixtures such as platelet rich plasma. Suitable antimicrobial agents include: bacitracin, biguanide, triclosan, gentamicin, minocycline, rifampin, vancomycin, cephalosporins, copper, zinc, silver, and gold. Nucleic acid molecules may include DNA, RNA, siRNA, miRNA, antisense or aptamers.

The implants may also contain allograft material and xenograft materials, including acellular dermal matrix material and small intestinal submucosa (SIS). In an embodiment, the implants may contain a vascular pedicle or other tissue mass. The vascular pedicle or other tissue mass are preferably autologous tissues.

In another embodiment, the implants may incorporate systems for the controlled release of the therapeutic or prophylactic agents.

In an embodiment, the implants are coated with allograft or xenograft tissue and cells prior to implantation, during implantation, or after implantation, or any combination thereof. In a particularly preferred embodiment, the implants are coated with autologous tissue and cells from the patient prior to implantation, during implantation, or after implantation, or any combination thereof. The autologous tissue and cells are preferably one or more of the following: autologous fat, fat lipoaspirate, fat tissue, injectable fat, adipose tissue, adipose cells, fibroblast cells, and stem cells, including human adipose tissue-derived stem cells, also known as preadipocytes or adipose tissue-derived precursor cells, and fibroblast-like stem cells. In one preferred embodiment, the implants may be coated with autologous tissue and cells as described herein, and may also further comprise a vascular pedicle or other tissue mass. As will be evident herein, the lattice structures of the implants are designed to create not only a shape for the implant, such as a breast implant, but also a large surface area that can retain the autologous tissue and cells to encourage tissue in-growth.

III. Methods for Preparing Implants from Skeletal Polyhedron Unit Cells, Coiled Unit Cells, Mesh Unit Cells and Foam Unit Cells A variety of methods can be used to manufacture the implants.

A. Implant Shapes

In an embodiment, the implants are designed so that when manufactured, they are three-dimensional.

Their shape allows the surgeon to increase tissue volume, fill voids, reconstruct lost or missing tissue or tissue structures, contour tissues, augment tissues, restore tissue or organ function, support or repair damaged tissue structures, enhance an existing tissue structure, increase soft tissue volume, and reshape parts of the body. For example, the implants can be used to reshape, replace or repair the breast, nipple, face and buttocks. In an embodiment, the implants allow the shape of soft tissue structures to be altered, or sculpted, without the use of permanent implants.

Within the scope described herein, it should be understood that there are a plurality of implant shapes and dimensions, and that the invention is not limited with regard to the three-dimensional shape and dimensions of the implant, except where recited in the appended claims. The implants can be assembled or printed to have any size and shape suitable for use as an implant. For example, implants can easily be prepared that have three-dimensional shapes such as a: sphere, hemisphere, cylinder, cone, dome, cuboid, tetrahedron, triangular or square prism, dodecahedron, torus, and ellipsoid, and custom shapes can be produced optionally with the assistance of computer-aided design. For example, one can produce cylinder shaped implants for the reconstruction of a nipple, or a dome shaped implant for the reconstruction of a breast. The dimensions of the implant may be sized to augment tissue volume, to substitute for prior tissue volume, to change the volumetric distributions of tissue, to change the appearance of tissues, or to replace existing tissue volume with a smaller volume.

In a preferred embodiment, implants are provided in shapes that can be used to alter the soft tissue volume of a breast without the use of a permanent breast implant, such as a silicone breast implant. In embodiments, the implants can be prepared in shapes and sizes for use in augmenting the size of a breast, replacing the tissue volume and shape of the breast following a mastectomy procedure, and to produce a specific appearance of the breast. For example, the implant can be prepared so that when implanted in the breast it produces a breast with a specific ratio of upper pole volume (UPV) to lower pole volume (LPV). In embodiments, the implant is a breast implant that has volumetric dimensions such that implantation of the implant results in a breast with an UPV of 25-35% of total breast volume, and LPV of 65-75% of total breast volume. In addition to sculpting the breast with specific volumetric ratios of tissue in the upper and lower poles, the dimensions and shape of the implant can also be chosen to provide very desirable shapes of the lower pole, upper pole, and extent of projection of the breast from the chest wall. In embodiments, the implants are breast implants designed so that (a) the lower pole of the breast has a very attractive lower pole curvature, specifically an attractive convex shape, (b) the upper pole of the breast has a straight or slightly concave curvature, and (c) the distance the breast projects from the breast wall is defined. It will therefore be apparent that the implants of the invention can be used to produce a very attractive reconstructed breast by having specific shapes that (i) define the ratio of the UPV to the LPV; (ii) define the curvatures of the upper and lower poles; (iii) define the extent of projection of the breast from the chest wall; and (iv) define the angulation of the nipple on the breast.

Additional shapes for the implant are set forth in U.S. patent application Ser. No. 16/262,018, filed Jan. 30, 2019 and entitled "FULL CONTOUR BREAST IMPLANT".

Implants designed for use in the breast can be prepared in sizes large enough to allow for their use in mastopexy and breast reconstruction. These implants are wide enough to span the width of a breast. In an embodiment, there are four sizes and shapes of implants used in breast surgery, namely, small, medium, large, and x-large. Four dimensions of these implants are shown in Table 1, wherein IMF-UP is the longitudinal distance between the implant's lowest point in the breast (which will be located nearest the inframammary fold (IMF) of the breast after implantation) and highest point in the breast, (which will be located nearest the intersection between the breast and chest wall in the upper pole after implantation), MD-LT is the width of the implant measured from the medial to lateral side of the implant, CHST-NAC is the maximum protrusion distance of the implant when implanted on the chest wall, and LP Radius is the radius of curvature of the implant in the lower pole. As is evident from Table 1, the implants for breast surgery may have an IMF-UP distance of 12-20.8 cm, a MD-LT dimension of 10.8-19.2 cm, CHST-NAC dimension of 5-11.9 cm, and a LP radius of 4.2-7.6 cm. The dimensions of the implant in the region giving shape to the upper pole can vary. In this region, the implant shape is preferably slightly concave or straight.

TABLE 1

Dimensions of breast implants

| Size | IMF-UP (cm) | MD-LT (cm) | CHST-NAC (cm) | LP Radius (cm) |
|---|---|---|---|---|
| Small | 12-14 | 10.8-12.5 | 5-6.4 | 4.2-4.6 |
| Medium | 14-16.2 | 12.5-14.5 | 6.4-7.9 | 5-5.4 |
| Large | 16.2-18.5 | 14.5-16.7 | 7.9-9.6 | 5.8-6.4 |
| X-Large | 18.5-20.8 | 16.7-19.2 | 9.6-11.9 | 6.8-7.6 |

Figure 9A:
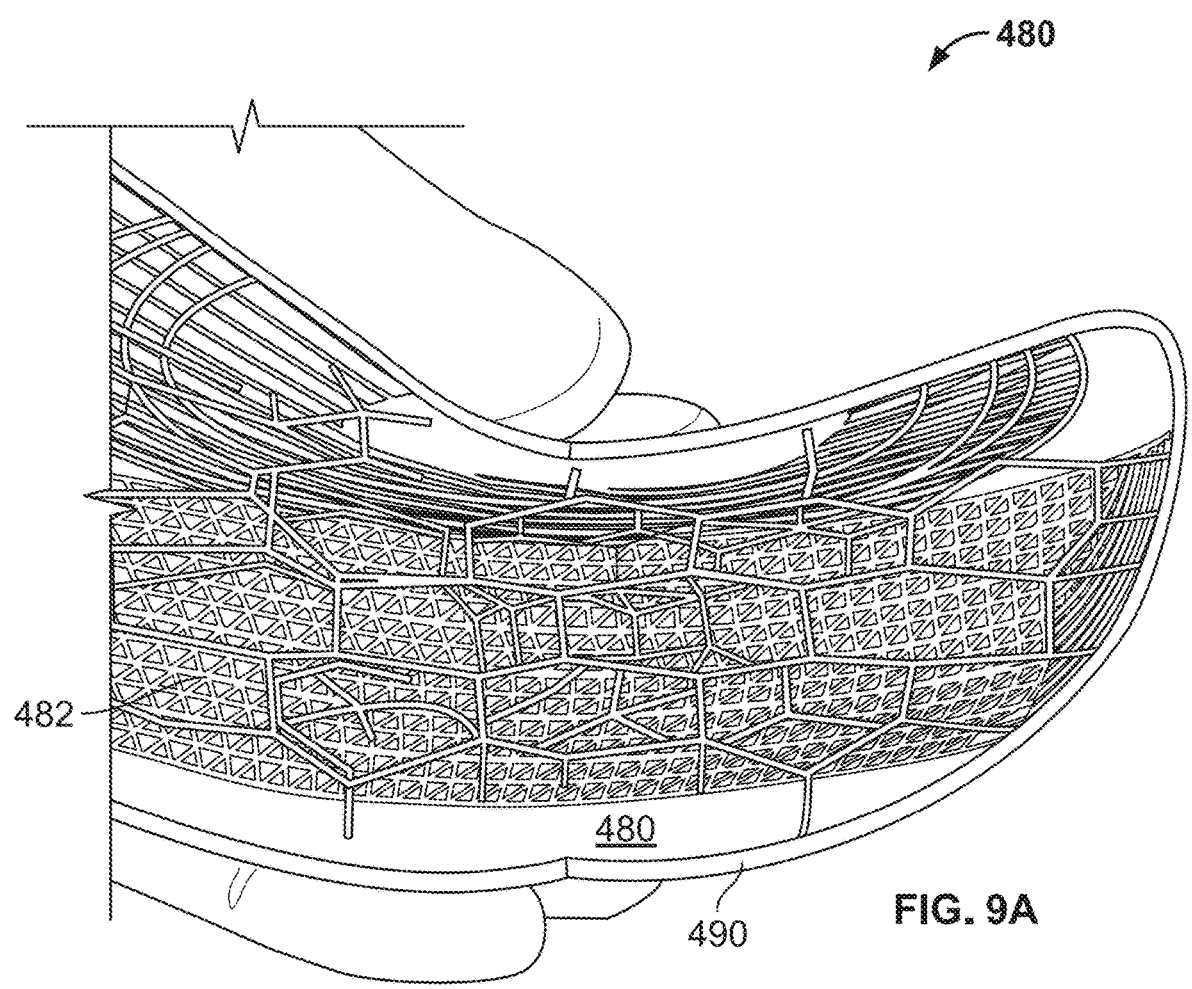
FIG. 9A is side view of an absorbable breast implant comprising skeletal polyhedron unit cells and a porous outer shell in accordance with an embodiment of the invention.
Figure 9B:
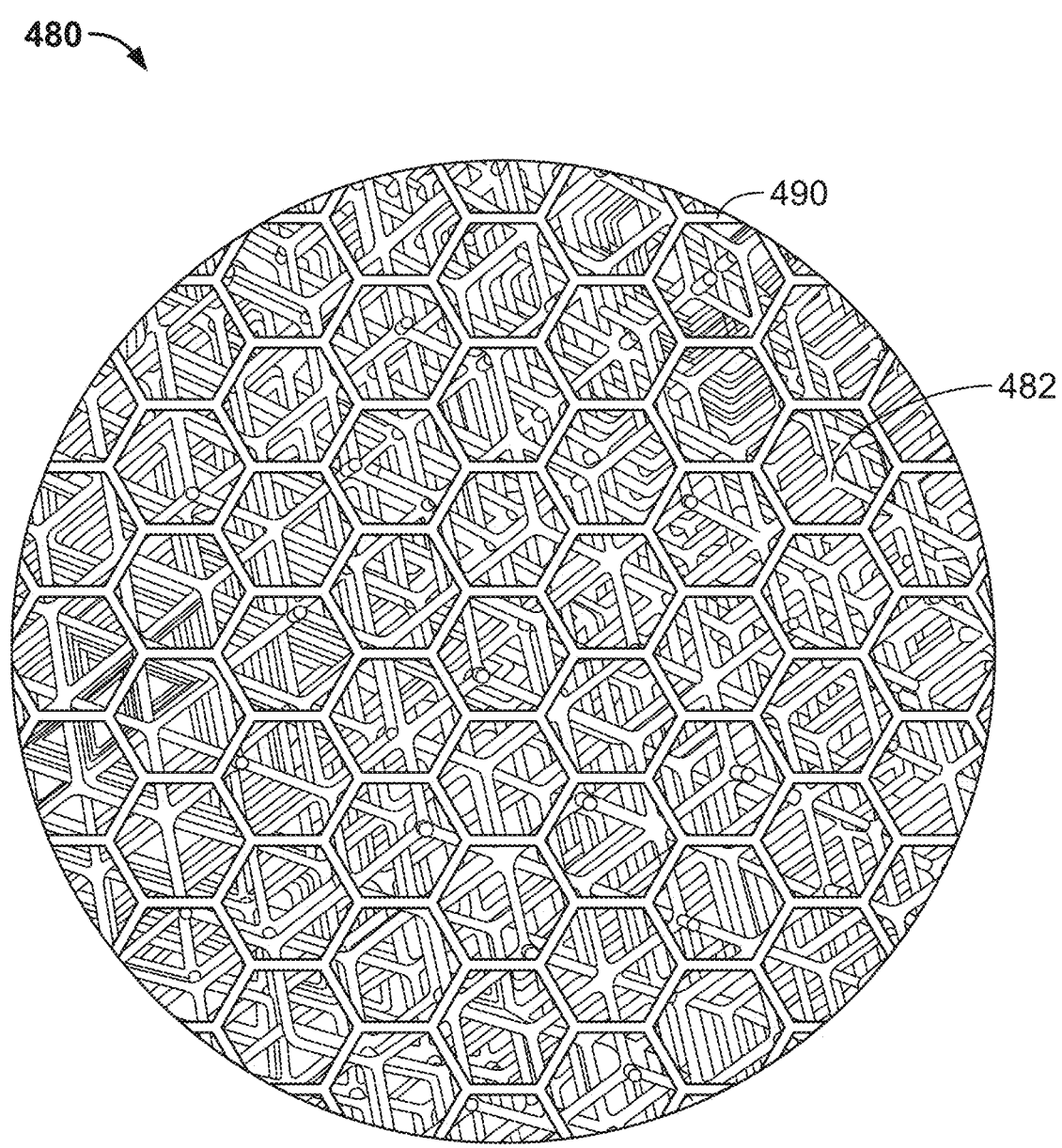
FIG. 9B is a top view of the implant shown in FIG. 9A showing the porous outer shell.

In embodiments, implants may be prepared with outer porous shells. For example, FIGS. 9A and 9B show how a breast implant can be constructed with skeletal polyhedron unit cells, and a porous outer shell. FIG. 9A shows a cross-section of the implant 480 with the unit cells 482 visible inside a porous outer shell 490 of the implant, and FIG. 9B shows the top of the porous outer membrane 490 covering the implant. The implant has a large surface area that can be coated, for example, with autologous fat, cells, collagen or bioactive agents.

B. Unit Cells

Implants comprising lattices with different shapes can be produced using the same or different types of unit cells. The unit cells may be assembled to form lattices, or 3D printed to form lattices. The lattices may comprise 2 or more unit cells, but more preferably 5, 10, 15, 20, 25, 30, 35, 40, 45, 50, 100, 1,000, 10,000 or more unit cells. A unit cell of the lattice is joined to one or more unit cell that may be of the same type, or a different type. The unit cells are hollow or porous such that lattices formed from the unit cells fill a defined volume, and create space-occupying structures. In one embodiment, the unit cells have pores with widths or diameters of 100 µm to 1 mm, and more preferably 250 µm to 750 µm. In another embodiment, the unit cells incorporated into a lattice may have the same sized pores, or a mixture of pore sizes. The lattices of the implants, made from the unit cells, have low volumetric densities that provide large surface areas and void volumes. The dimensions of the unit cells make it possible to form low volumetric density lattices from the unit cells that can be colonized by cells and invaded by tissue, blood vessels, or combinations thereof. The dimensions of the unit cells also make it possible to coat the lattices of the implants with allograft or xenograft tissue and cells, preferably autologous tissue and cells, including, but not limited to, autologous fat, fat lipoaspirate, lipo-filling, injectable fat, adipose cells, fibroblast cells, and stem cells. In a preferred embodiment, the dimensions of the unit cells make it possible to coat the inside of the lattice formed from the unit cells with fat, fat lipoaspirate, injectable fat, adipose cells, fibroblast cells, and stem cells. The unit cell dimensions are also designed to allow the lattice to be coated with collagen and or hyaluronic acid or derivative thereof. The cells and other compositions, such as collagen and hyaluronic acid, may be coated on the lattices prior to implantation, after implantation, or both before and after implantation. Preferably, the dimensions of the unit cells are large enough to allow needles to be inserted into the lattice structures in order to deliver bioactive agents, cells, fat and other compositions by injection. In embodiments, the lattices are constructed with unit cells that allow needles with gauges of 12-21 to be inserted into the unit cells of the lattices. This property allows the lattices to be loaded with cells, tissue, collagen, bioactive agents and additives, including fat, using a syringe and without damaging the lattice. Preferably, the lattices allow insertion of needles with outer diameters of 0.5 to 3 mm.

The sizes and shapes of the unit cells may be selected to provide different types of lattices with different volumetric densities. The properties of the implant lattices formed from the repeating unit cells are highly predictable, and can be predicted based on the dimensions of the unit cells, and the materials used to prepare the unit cells. Unit cells with different physical properties may be prepared by selection of the dimensions of the unit cells, geometries of the unit cells, and the material used to prepare the unit cells. Selecting specific unit cell dimensions and materials makes it possible to produce lattices from the unit cells with properties ranging from stiff, hard, or rigid, to elastic, soft, or compressible. In embodiments, the mechanical properties of the lattices may be varied without changing the shape of the unit cells, but instead by varying the diameter or width of the struts or fiber of the unit cells. For example, the required strut thickness or diameter of a given unit cell, made from a given polymer, can be calculated if a desired mechanical property is known, such as elastic modulus or compressive strength. In a preferred embodiment, the dimensions and materials of unit cells are selected such that implant lattices prepared from the unit cells have properties that are similar to those of the soft tissues where the implants are implanted. For example, the dimensions and materials of the unit cells may be selected to provide implant lattices that have mechanical properties similar to those of breast tissue. In another preferred embodiment, the unit cells can be compressed, and optionally recover their original shape when the compressive force is released.

i. Skeletal Polyhedron Unit Cells

In embodiments, the unit cells are skeletal polyhedrons with edges and vertices formed from polymeric struts or fibers. The edges and vertices, or struts/fibers, of the skeletal unit cells may have different dimensions, thicknesses, lengths, angles, and may be stiff, rigid, flexible, elastic, spring-like, and may be made from oriented or unoriented polymers. In an embodiment, the lattices may be prepared from skeletal unit cells with one or more of the following shapes: tetrahedron, cuboid, pentahedron, hexahedron, heptahedron, octahedron, icosahedron, decahedron, dodecahedron, tetradecahedron, and prisms, antiprisms, and truncated polyhedra thereof. Examples of unit cells in the shape of prisms, antiprisms and truncated polyhedral are a hexagonal prism, an octagonal antiprism, and a truncated dodecahedron. In an embodiment the skeletal unit cells are formed from elongated polyhedra. In a preferred embodiment, the skeletal unit cells have 4, 6, 8, 12 or 20 faces. In a particularly preferred embodiment, the skeletal unit cells are dodecahedrons, even more preferably rhombic dodecahedrons. Thus, for example, unit cells with rhombic dodecahedron shapes can be formed into the lattice of an implant, and the implant implanted for example in the breast, nipple, face or buttock. Or the lattice may be formed from unit cells with octagonal shapes. In other embodiments, the lattice may be made from two or more different skeletal unit cells, for example, a combination of dodecahedron and octagonal shapes.

In embodiments, the implants are formed from skeletal polyhedron wherein the edges and vertices of the unit cells forming the skeletal polyhedron have diameters or widths of 0.025 to 3 mm, more preferably 0.1 to 2 mm, and even more preferably from 0.15 to 1 mm. In embodiments, the edges and vertices of the unit cells forming the skeletal polyhedron have breaking loads of 0.1 to 200 N, more preferably 1 to 100 N, and even more preferably 2 to 50 N. In embodiments, the edges and vertices of the unit cells forming the skeletal polyhedron have an elongation at break of 22% to 1,000%, and more preferably 100% to 700%. In embodiments, the edges and vertices of the unit cells forming the skeletal polyhedron have an elastic modulus value of 0.05 to 10 GPa, more preferably 0.1 to 3 GPa, and even more preferably 0.2 to 0.8 GPa. The diameters, widths, breaking loads, elongation at break, and elastic modulus values of the edges and vertices of the unit cells may be the same throughout the skeletal polyhedron or unit cells, or these values may be different through the skeletal polyhedron or unit cells. Polymeric struts forming the edges and vertices of the unit cells preferably have one or more of the following properties: (i) breaking load of 0.1 to 200 N, (ii) elongation at break of 22 to 1,000%, and (iii) elastic modulus of 0.05 to 10 GPa.

In embodiments, the implants formed from skeletal polyhedron have an elastic modulus of 0.01 kPa to 290 MPa, more preferably from 0.1 kPa to 10 MPa, and even more preferably from 0.1 kPa to 1 MPa or 0.1 kPa to 100 kPa, and the polymeric struts or fibers of the unit cells forming the skeletal polyhedron have one or more of the following properties: (i) diameters of 0.025 to 3 mm, more preferably 0.1 to 2 mm, and even more preferably 0.15 to 1 mm; (ii) initial breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa.

In embodiments, the implant is a breast implant formed from a skeletal polyhedron and the implant has an elastic modulus of 0.01 kPa to 290 MPa, more preferably from 0.1 kPa to 10 MPa, and even more preferably from 0.1 kPa to 1 MPa or 0.1 kPa to 100 kPa, and the polymeric struts or fibers of the unit cells forming the skeletal polyhedron have one or more of the following properties: (i) diameters of 0.025 to 3 mm, more preferably 0.1 to 2 mm, and even more preferably 0.15 to 1 mm; (ii) initial breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa.

With reference to FIG. 1, a breast implant 10 is shown comprising a lattice made from connected unit cells that are skeletal rhombic dodecahedrons. The implant 10 has a low volumetric density that provides a large surface area and void volume.

FIGS. 2A-2D illustrate various views of a skeletal rhombic dodecahedral unit cell 20 used to create the lattice implant 10 shown in FIG. 1. The skeletal rhombic dodecahedral unit cell 20 has 12 open faces/space formed by edges and vertices of the unit cell that are made from polymeric struts 22. The inside of the unit cell is hollow.

Figure 3:
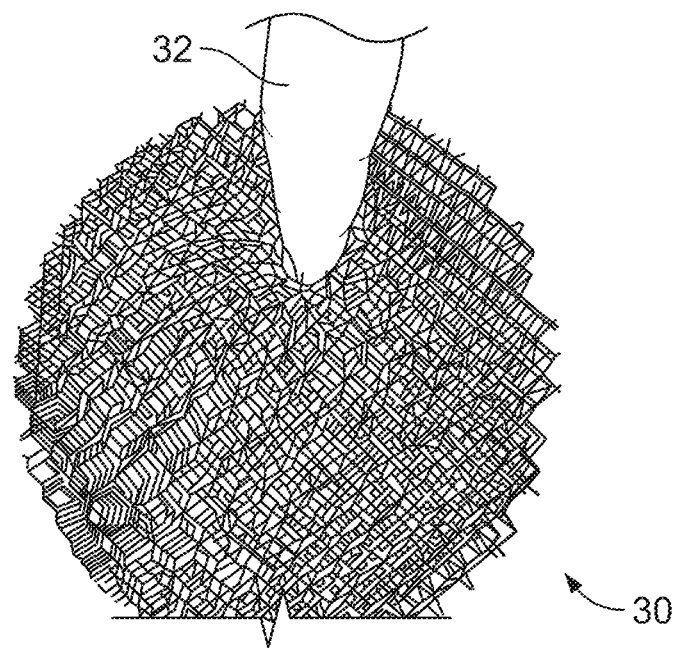
FIG. 3 is an illustration of the implant shown in FIG. 1 being compressed by finger.

FIG. 3 illustrates comprising lattices with desirable properties by preparing unit cells with specific dimensions, and with specific polymeric materials. In the example shown in FIG. 3, a breast implant 30 comprising a lattice is shown, wherein it is evident that the lattice is compressible by relatively light pressure from a finger 32 is sufficient to compress the lattice structure. When the finger is removed, the lattice resumes the original shape shown in FIG. 1. An implant comprising a compressible lattice is particularly suitable for use in the breast since the compressibility of the lattice can be engineered to mimic the properties of breast tissue. Thus, a patient will not feel a hard implant in the breast when the breast is massaged.

With reference again to FIGS. 2A-2D, the lengths (L) of the struts or fibers in the skeletal polyhedron unit cells are preferably 1 to 300 mm, more preferably 2 mm to 10 mm, and even more preferably 3 mm to 8 mm. In embodiments, the struts or fibers are long enough to form unit cells that allow the insertion of a needle into the lattice made of the unit cells with an outside needle diameter (OD) of 0.5 to 3 mm.

The height (H) of a unit cell may vary. In embodiments, the height (H) ranges from 1 to 500 mm, more preferably 5 to 20 mm, and even more preferably 12 to 18 mm.

The width (W) of the struts or diameter of the fibers in the skeletal polyhedron unit cells are preferably 50 μm to 5 mm, more preferably 150 μm to 2 mm, and even more preferably 200 μm to 1.5 mm or 500 μm to 1 mm. One advantage of the implant design is that the strut width or fiber diameter, and strut or fiber length, needed to produce a lattice with a specific elastic modulus or other mechanical property can be calculated for a given material.

In one particularly preferred embodiment, the skeletal units cells are compressible, and even more preferably can recover to their original dimensions after compression. A particularly preferred embodiment is a compressible breast implant comprising skeletal unit cells that can recover its original dimensions following compression. Implants with different shapes may also be produced using the same or different unit cells wherein the unit cells are skeletal unit cells.

ii. Units Cells with Coils or Springs

Figure 4:
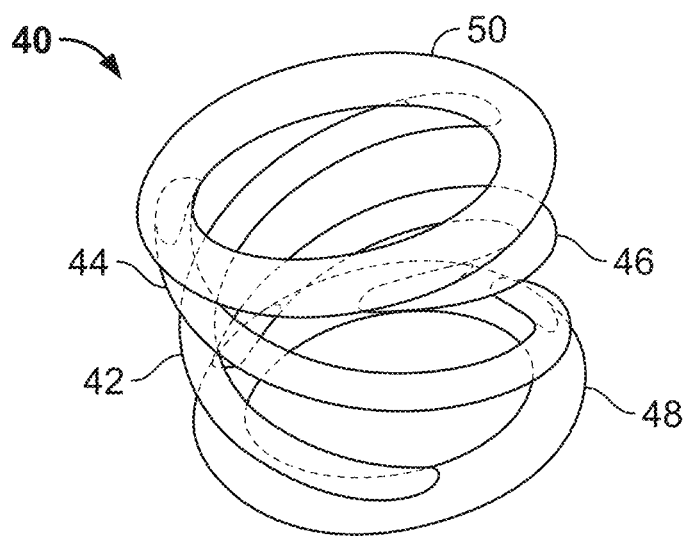
FIG. 4 is a perspective view of a coiled cylindrical unit cell in accordance with an embodiment of the invention.

In other embodiments, the unit cells that are used to form the lattice of the implant are coils, springs or spirals formed from polymers. An example of a unit cell with coils and springs is shown in FIG. 4. In this example, the unit cell is a coiled cylindrical unit cell 40 consisting of three helical struts or wires 42, 44, 46 supporting a top and a bottom ring 48, 50. The top and bottom rings of the unit cell shown in FIG. 4 have an outer diameter of 10 mm, inner diameter of 8 mm, and 2 mm round cross-sections. The helical struts or wires are angled at 120 degrees from each other at a constant pitch of 0.75 per centimeter. In an embodiment, the outside diameters of the unit cells that are coils and or springs range from 2 to 30 mm, and more preferably from 5 to 15 mm. In an embodiment, the outer diameter of the helical struts or wires may be 0.2 to 3 mm. In an embodiment, the helical struts of these unit cells may be angled at 10 to 180 degrees from each other, and the pitch of the helical struts may be 0.5 to 5 per cm. The number of helical struts of the unit cell is preferably from 1 to 20, but more preferably from 2 to 5.

The required dimensional specifications of the unit cells comprising coils or springs may be calculated for a given material in order to provide lattices with specific mechanical properties, such as a specific elastic modulus or compressive strength. In one particularly preferred embodiment, the unit cells made from coils and or springs are compressible, and even more preferably can recover to their original dimensions after compression. Implants with different shapes may also be produced using the same or different unit cells wherein the unit cells are coils and or springs.

In embodiments, the implants are formed from unit cells comprising coils or springs, and the coils or springs have diameters or widths of 0.025 to 3 mm, more preferably 0.1 to 2 mm, and even more preferably from 0.15 to 1 mm. In embodiments, the coils or springs of the unit cells forming the skeletal polyhedron have breaking loads of 0.1 to 200 N, more preferably 1 to 100 N, and even more preferably 2 to 50 N. In embodiments, the coils or springs of the unit cells forming the skeletal polyhedron have an elongation at break of 22% to 1,000%, and more preferably 100% to 700%. In embodiments, the coils or springs of the unit cells forming the skeletal polyhedron have an elastic modulus value of 0.05 to 10 GPa, more preferably 0.1 to 3 GPa, and even more preferably 0.2 to 0.8 GPa. The diameters, widths, breaking loads, elongation at break, and elastic modulus values of the coils or springs of the unit cells may be the same throughout the skeletal polyhedron or unit cells, or these values may be different through the skeletal polyhedron or unit cells. The coils or springs of the unit cells preferably have one or more of the following properties: (i) breaking load of 0.1 to 200 N, (ii) elongation at break of 22 to 1,000%, and (iii) elastic modulus of 0.05 to 10 GPa.

In embodiments, the implants formed from a lattice of the coils or springs have an elastic modulus of 0.01 kPa to 290 MPa, more preferably from 0.1 kPa to 10 MPa, and even more preferably from 0.1 kPa to 1 MPa or 0.1 kPa to 100 kPa, and the coils or springs forming the lattices have one or more of the following properties: (i) diameters of 0.025 to 3 mm, more preferably 0.1 to 2 mm, and even more preferably 0.15 to 1 mm; (ii) initial breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa.

In embodiments, the implant is a breast implant formed from a lattice of coils or springs and the breast implant has an elastic modulus of 0.01 kPa to 290 MPa, more preferably from 0.1 kPa to 10 MPa, and even more preferably from 0.1 kPa to 1 MPa or 0.1 kPa to 100 kPa, and the coils or springs forming the lattice have one or more of the following properties: (i) diameters of 0.025 to 3 mm, more preferably 0.1 to 2 mm, and even more preferably 0.15 to 1 mm; (ii) initial breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa.

Figure 5:
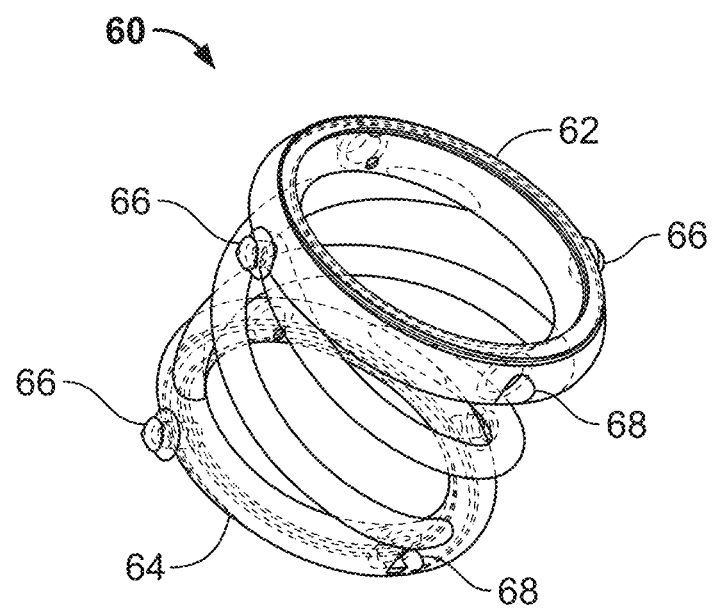
FIG. 5 is a perspective view of a coiled unit cell including fasteners for assembling unit cells together in accordance with an embodiment of the invention.

In a preferred embodiment, the unit cells made from coils and or springs further comprise fasteners that can be used to assemble the unit cells into a lattice. One example of unit cells 60 made from coils and springs that further comprise fasteners is shown in FIG. 5. In this example, the top and bottom rings 62, 64 of the unit cells comprise fasteners. The fasteners can use any suitable mechanism that allows the unit cells to be joined together. In the example shown in FIG. 5, the unit cells comprise male 66 and female 68 connectors that may be joined together to assemble the unit cells into a lattice. In FIG. 5, a male and female fastener is visible in both the upper and lower rings of the unit cell separated by an angle of 90 degrees. Although not visible in FIG. 5, the unit cell shown comprises two male connectors and two female connectors in each of the top and bottom rings of the unit cell, with the male and female connectors alternating and positioned at 90 degree intervals. The number of fasteners used to connect the unit cells can be more or less than 4 on the upper and lower rings of the unit cells, but preferably the upper and lower rings each comprise 2 male and 2 female connectors alternating at 90 degree intervals. If desired, the fasteners may also be positioned on the helical struts of the unit cells.

iii. Mesh Unit Cells

In yet another embodiment, the unit cells are formed from mesh and fiber. The unit cells may have a top plate formed from mesh and a bottom plate formed from mesh. The top plate and the bottom plate are joined together by fiber to form the mesh unit cell. Preferably, the top plate and bottom plate are joined by interlacing of fiber, more preferably, by interlacing the top plate and bottom plate with monofilament fiber.

Figure 12:
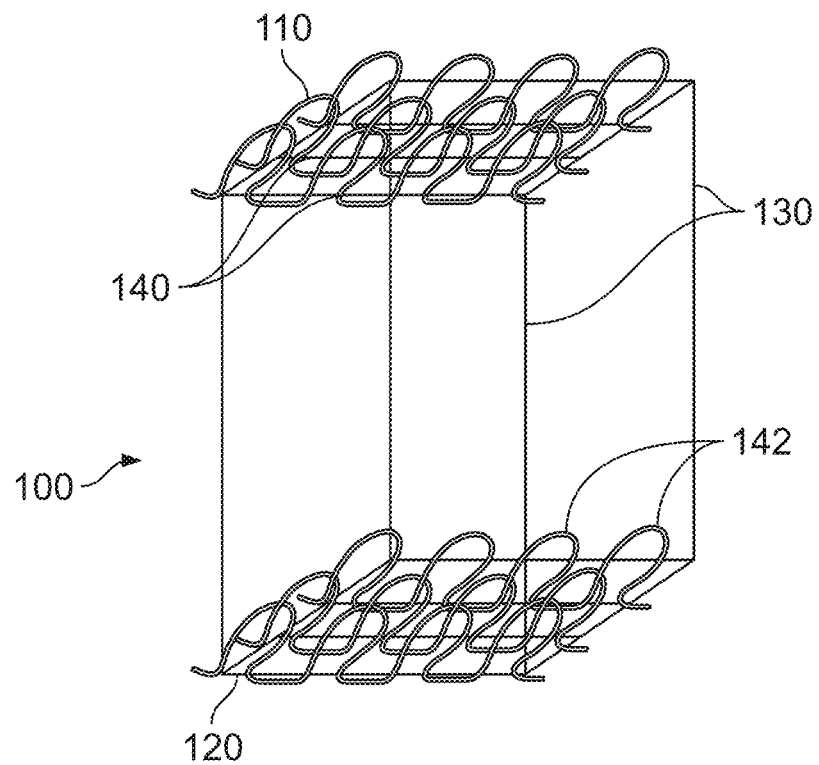
FIG. 12 is a diagram of a mesh unit cell in accordance with an embodiment of the invention.
Figure 13:
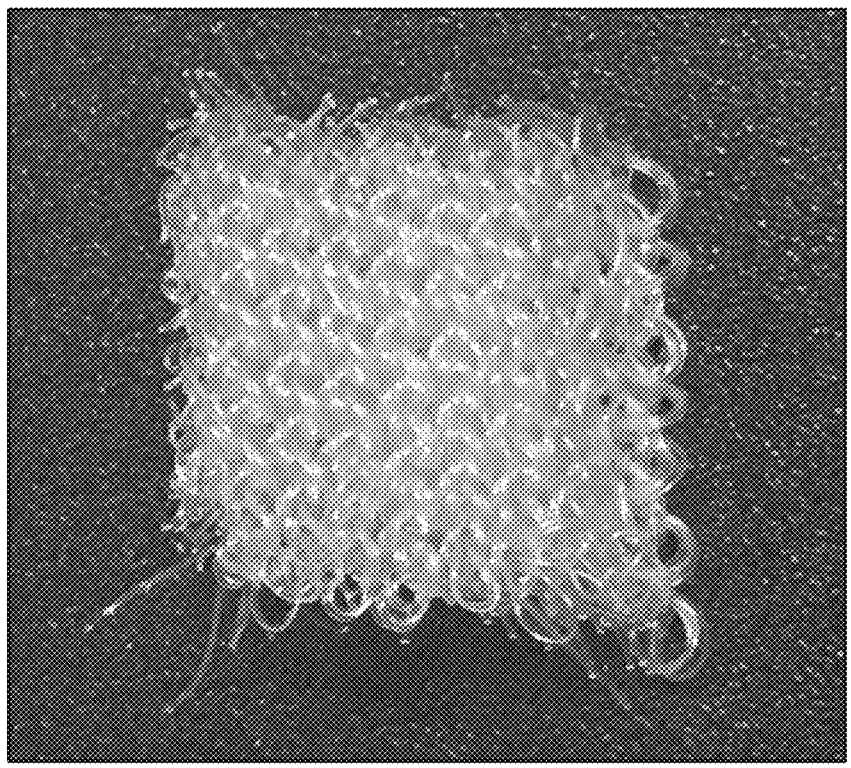
FIG. 13 is a top view of a cuboid shaped compressible unit cell in accordance with an embodiment of the invention.
Figure 14:
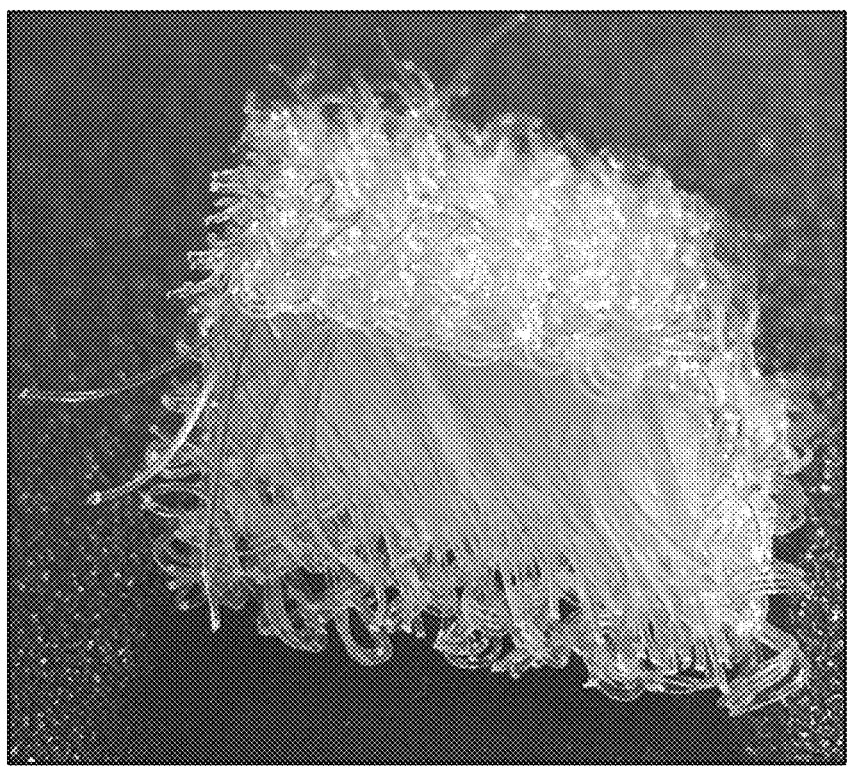
FIG. 14 is a side perspective view of the cuboid shaped compressible unit cell shown in FIG. 13.
Figure 15:
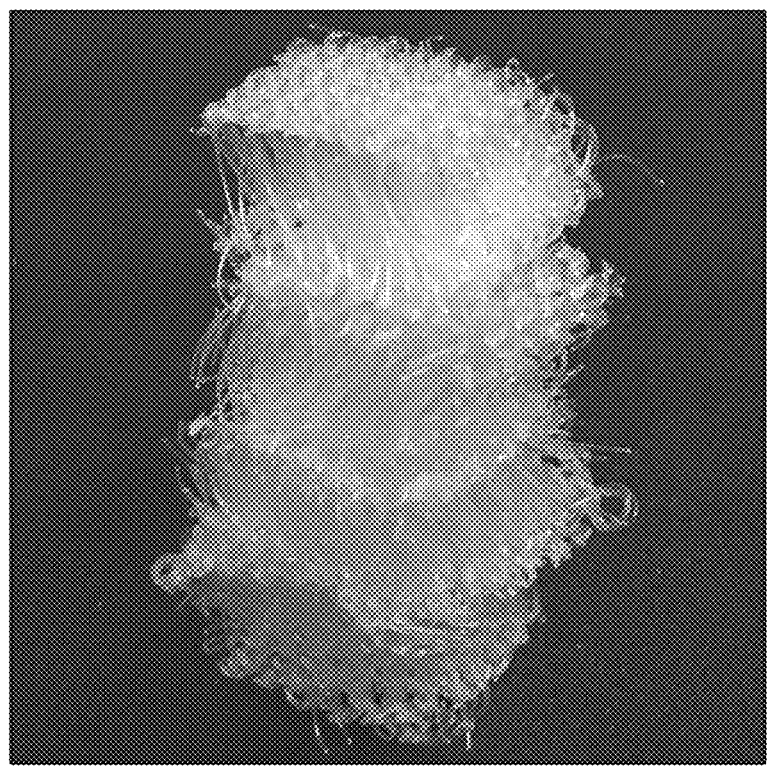
FIG. 15 is a side perspective view of four cuboid shaped compressible unit cells stitched together to form a compressible assembly unit in accordance with an embodiment of the invention.

FIG. 12 is a diagram of a mesh unit cell 100 showing a top plate 110 and a bottom plate 120, and struts 130 joining the top and bottom plates. The top and bottom plates are formed from mesh. Fiber inlay 140 from the mesh is shown on the top and bottom plates, and the interlaced loops 142 of the mesh are also shown. The struts shown in FIG. 12 are preferably formed from fiber, more preferably monofilament fiber. The mesh unit cells have low volumetric density that provides a large surface area and void volume. The top and bottom plates and the struts may have different dimensions, angles and lengths, and may be stiff, rigid, flexible, elastic, spring-like, and may be made from oriented or unoriented polymers. The mesh unit cell may be formed in any suitable shape. In an embodiment, the mesh unit cells have polyhedra shapes, including elongated polyhedra shapes. In a preferred embodiment, the mesh unit cell has six faces. In a particularly preferred embodiment, the mesh unit cell is a cuboid. The inside of the mesh unit cell may be hollow, or may comprise further fibers. For example, the mesh unit cell may comprise further fibers that join the top and bottom plates. The mesh unit cell may also comprise further fibers located between the top and bottom plates that increase the surface area of the unit cell. The latter may result in an increased binding capacity of the unit cell, for example, to bind fat.

In a preferred embodiment, the mesh unit cells are compressible, and in an even more preferred embodiment the mesh unit cells are compressible and recover following compression. An implant with a lattice formed from compressible mesh unit cells is particularly suitable for use in the breast since the lattice so formed is compressible, and can be engineered to mimic the properties of breast tissue.

The length of the struts or fibers of the mesh unit cells are preferably 1 to 300 mm, more preferably 2 mm to 10 mm, and even more preferably 3 mm to 8 mm. In embodiments, the struts or fibers are long enough to form unit cells that allow the insertion of a needle into the lattice made of the unit cells with an outside needle diameter of 0.5 to 3 mm.

The diameters of the fibers used to prepare the mesh unit cells are preferably 20 µm to 2 mm, more preferably 50 µm to 1 mm, and even more preferably 80 µm to 500 µm or 100 µm to 250 µm.

In embodiments, the implants are formed from mesh unit cells with fiber, and the fiber has a breaking load of 0.1 to 200 N, more preferably 1 to 100 N, and even more preferably 2 to 50 N. In embodiments, the implants are formed from mesh unit cells with fiber, and the fiber has an elongation at break of 22% to 1,000%, and more preferably 100% to 700%. In embodiments, the implants are formed from mesh unit cells with fiber, and the fiber has an elastic modulus value of 0.05 to 10 GPa, more preferably 0.1 to 3 GPa, and even more preferably 0.2 to 0.8 GPa. The fibers forming the mesh unit cells preferably have one or more of the following properties: (i) breaking load of 0.1 to 200 N, (ii) elongation at break of 22 to 1,000%, and (iii) elastic modulus of 0.05 to 10 GPa.

In embodiments, the implants formed from mesh unit cells with fiber have an elastic modulus of 0.01 kPa to 290 MPa, more preferably from 0.1 kPa to 10 MPa, and even more preferably from 0.1 kPa to 1 MPa or 0.1 kPa to 100 kPa, and the fibers of the mesh unit cells have one or more of the following properties: (i) diameters of 0.025 to 3 mm, more preferably 0.1 to 2 mm, and even more preferably 0.15 to 1 mm; (ii) initial breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa.

In embodiments, the implant is a breast implant formed from mesh unit cells, and the implant has an elastic modulus of 0.01 kPa to 290 MPa, more preferably from 0.1 kPa to 10 MPa, and even more preferably from 0.1 kPa to 1 MPa or 0.1 kPa to 100 kPa, and the fibers of the mesh unit cells have one or more of the following properties: (i) diameters of 0.025 to 3 mm, more preferably 0.1 to 2 mm, and even more preferably 0.15 to 1 mm; (ii) initial breaking loads of 0.1 to 200 N, more preferably 1 to 100 N, and even more preferably 2 to 50 N; (iii) elongation at break values of 22% to 1,000%, and more preferably 100% to 700%; and (iv) elastic modulus values of 0.05 to 10 GPa, more preferably 0.1 to 3 GPa, and even more preferably 0.2 to 0.8 GPa.

iv. Foam Unit Cells

In a further embodiment, the unit cells are formed of foams, preferably compressible foams. The foam unit cells preferably comprise pores that are interconnected. The pores may be unisized (i.e., each pore has an equal size) or different sizes. The foam unit cells have a low volumetric density that provides a large surface area and void volume. The foam unit cells may be formed in any suitable shape. In an embodiment, the foam unit cells have polyhedra shapes, including elongated polyhedra shapes. In a preferred embodiment, the foam unit cell has six faces. In a particularly preferred embodiment, the foam unit cell is a cuboid.

In an embodiment, the foam unit cells further comprise male and female anchors. The anchors allow multiple unit cells to be joined together to form a lattice of an implant.

Figure 16A:
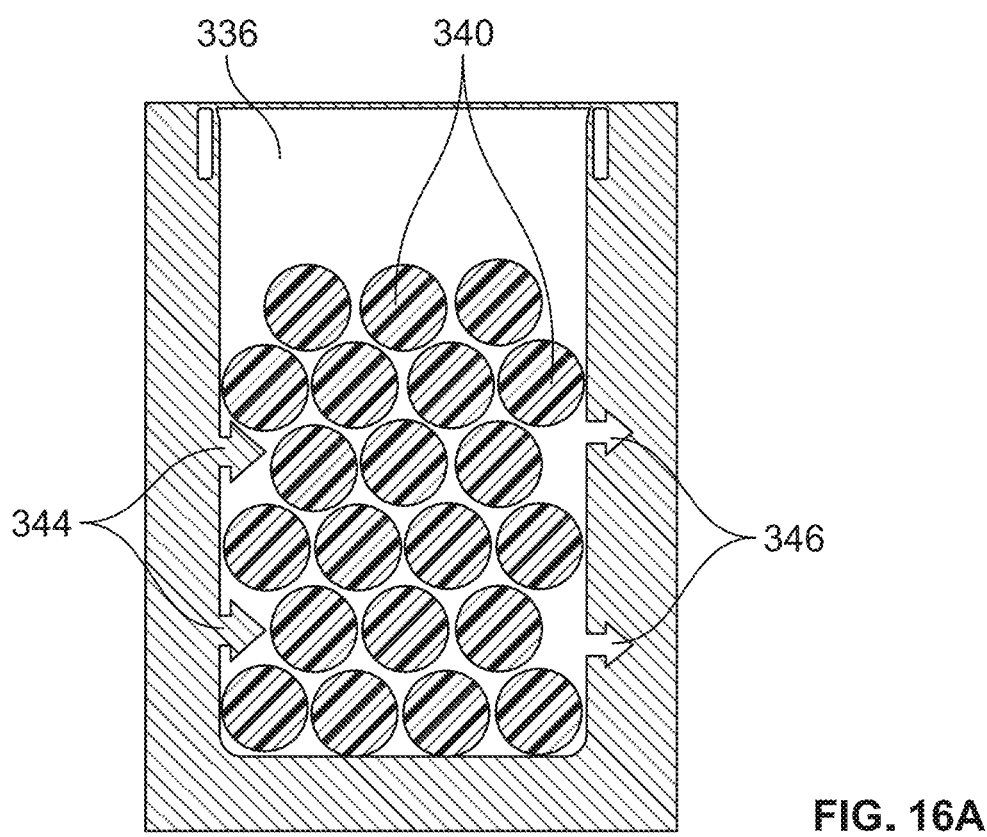
FIGS. 16A-16C are diagrams illustrating a process for forming a porous compressible foam unit in accordance with an embodiment of the invention.
Figure 16B:
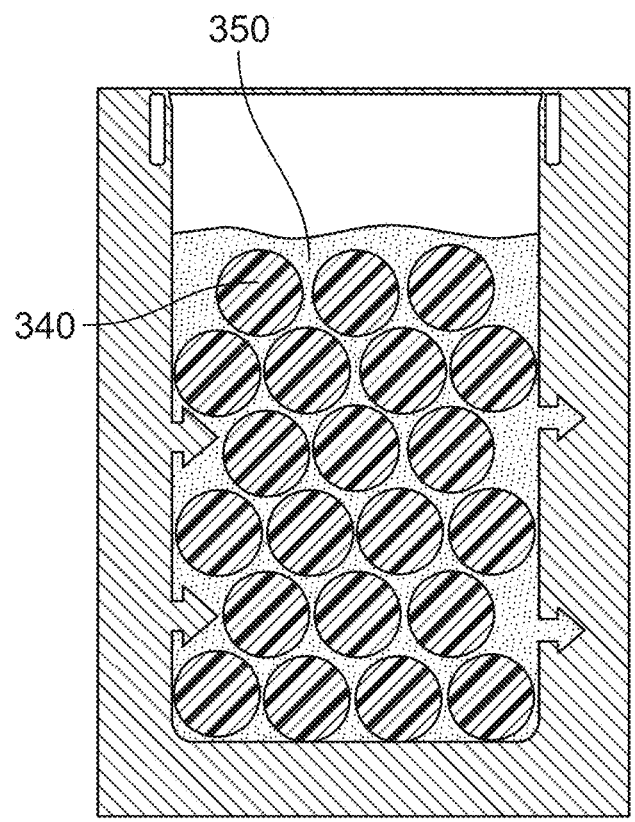
Figure 16C:
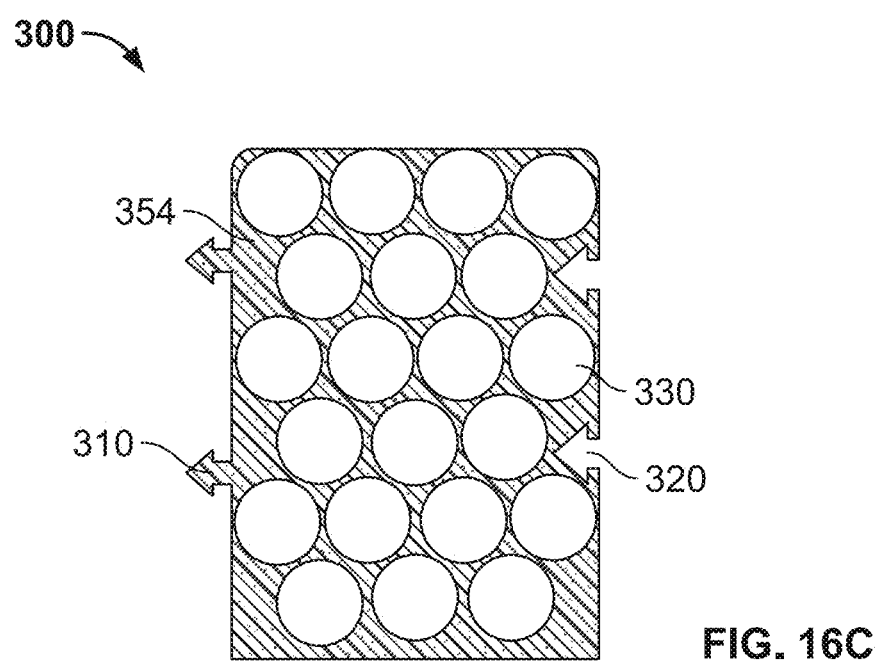

With reference to FIG. 16C, a cross-sectional diagram of a compressible foam unit cell 300 with male 310 and female 320 anchors showing pores 330 in the foam 340. The foam 340 is preferably formed from a polymer, and more preferably an absorbable polymer.

FIGS. 16A, 16B and 16C show one method for forming foam unit cells in accordance with one embodiment of the invention. Particularly, FIG. 16A shows a mold cavity 336 filled with leachable porogen beads 340. Optionally, the mold cavity may feature female formation anchor sites 344, and male formation anchor sites 346, described further herein.

With reference to FIG. 16B, the beads 340 are covered with a solution 350 of polymer in a volatile solvent. The solvent is allowed to evaporate leaving the porogen beads trapped in the polymer. The open foam unit cells 300 are formed by leaching the porogen beads trapped in the polymer as shown in FIG. 16C such that an array of pores 330 are left in the foam 354. Optionally, male 310 and female 320 anchors are created to assemble the foam units together as described herein.

An implant with a lattice formed from compressible foam unit cells is particularly suitable for use in the breast since the lattice so formed is compressible, and can be engineered to mimic the properties of breast tissue.

C. Construction of the Implants

A variety of methods can be used to manufacture the implants. The implants comprise lattices formed from two or more unit cells, but more preferably from multiple unit cells or a large number of unit cells. The unit cells repeat over the volume of the lattice. In embodiments, the implant's lattice is able to provide one or more of the following: (i) structural support, (ii) a scaffold for tissue ingrowth, (iii) a scaffold for delivering cells, tissues, collagen, hyaluronic acid, and bioactive agents, including fat, lipoaspirate, adipose cells, fibroblast cells, and stem cells (iv) a structure that can provide mechanical spacing, (v) a structure that can allow incorporation of a graft into the lattice structure, such as a vascular pedicle, (vi) a structure that can be coated with cells, tissues, collagen, hyaluronic acid, and bioactive agents, including fat, lipoaspirate, adipose cells, fibroblast cells, and stem cells on the inside of the lattice by injection using a needle, (vii) a structure with properties similar (meaning within ±50% of a property value) or the same as soft tissues, (viii) a structure with an elastic modulus that is within ±50%, more preferably ±25% of the elastic modulus value of breast tissue, (viii) a structure with a high strength relative to its volumetric density, (ix) a structure with a compressive design and or a spring design (meaning that the lattice may be deformed by a force and recover its original shape when the force is removed), and (x) a structure with anisotropic mechanical properties.

In one embodiment, the implant is formed by making a lattice of unit cells wherein the unit cells are coils and springs. In another embodiment, the implant is formed by making a lattice of unit cells wherein the unit cells are skeletal polyhedrons with edges and vertices formed from struts or fibers, and with hollow or porous interiors. Preferably, the skeletal polyhedron unit cells meet adjacent skeletal polyhedron cells at their corners to form lattices. In yet another embodiment, the implant is formed by making a lattice of mesh unit cells wherein the mesh unit cell comprises mesh on two opposite faces of the unit cell, and the meshes are joined by struts or fibers. In a further embodiment, the implant is formed by making a lattice of foam unit cells.

In a preferred embodiment, the implant's lattice is formed from unit cells wherein the unit cells are formed from polymers. The unit cells may be polymeric coils and springs, skeletal polyhedrons wherein the edges and vertices of the skeletal polyhedrons are formed from polymeric struts or fibers, or the unit cells may be polymeric meshes connected with polymeric fibers or the unit cells may be polymeric foams.

In a preferred embodiment, the implant is formed from a lattice of unit cells, wherein the unit cells have a low volumetric density providing an open pore network through the lattice and such that when a unit cell is placed in the center of the lattice, it will be surrounded by other unit cells. For example, if the unit cells of the lattice all have the shape of a dodecahedron with 12 faces, each face of the dodecahedron will be connected to 12 adjacent unit cells. Connecting the unit cells in this manner creates a lattice network wherein there is a continuous path through the lattice which encourages and allows tissue ingrowth into the lattice structure. The continuous path also allows the entire lattice structure to be coated with one or more of the following: bioactive agents, collagen, hyaluronic acid, additives, cells and tissue, including fat and fat cells. The number of unit cells forming the lattice will depend in part upon the volume of the lattice needed, and the unit volume of the unit cells. For example, a lattice with a volume of 500 $cm^3$ made from identical unit cells with a volume of 1 $cm^3$ would contain up to 500 unit cells.

The lattices of the implants may be defined by their volumetric density. In a preferred embodiment, the volumetric density of the implant's lattice, which is the ratio of volume of material used to make the lattice to the volume of voids in the lattice is 1-50%. In a more preferred embodiment, the volumetric density of the lattices is between 1% and 25%, and in an even more preferred embodiment the volumetric density of the lattices is between 1% and 17%. For clarity of definition only, a lattice with a volumetric density of 25% has 25% material by volume and 75% void space. The volumetric density of the lattice refers to the volumetric density prior to the addition of cells or other substances. Lattices with low volumetric densities, for example, less than 50% are preferred because they provide a large void space that can be occupied, for example, by cells, tissues, collagen, and bioactive agents, including fat, lipoaspirate, adipose cells, fibroblast cells, and stem cells. In one embodiment, 25% to 100% and more preferably 75% to 100% of the void space is filled with one or more of the following: cells, tissues, collagen, and bioactive agents, including fat, lipoaspirate, adipose cells, fibroblast cells, and stem cells.

The struts, fibers, coils and springs of the unit cells may be fabricated by any suitable methods. A preferred method for fabricating the unit cells is 3D printing. 3D Printing is a computer controlled process whereby a three-dimensional object can be fabricated from a 3D CAD (Computer Aided Design) model using an additive manufacturing approach. Objects may be fabricated by depositing, joining, or solidifying material, typically a plastic or metal. 3D printing may be used to fabricate the unit cells, and may also be used for the fabrication of the lattice structure. The latter method is particularly preferred when the lattice of the implant comprises unit cells that are skeleton polyhedrons, but may also be used to fabricate the unit cells comprising coils or springs. Suitable 3D printing techniques include selective laser melting (SLM), melt extrusion deposition (MED), fused pellet deposition (FPD), fused filament fabrication, printing of slurries and solutions using a coagulation bath, and printing using a binding solution and granules of powder. In an embodiment, the lattices of the implants are formed by 3D printing of an absorbable polymer, and more preferably by 3D printing of one or more of the following: poly-4-hydroxybutyrate and copolymer, and poly(butylene succinate) or copolymer, optionally wherein these polymers and copolymers have been cross-linked. In a particularly preferred embodiment, the implant is a breast implant, and the unit cells and or lattice of the implant are formed by 3D printing with one or more of the following: poly-4-hydroxybutyrate and copolymer, and poly(butylene succinate) or copolymer, optionally wherein these polymers and copolymers have been cross-linked.

Figure 6:
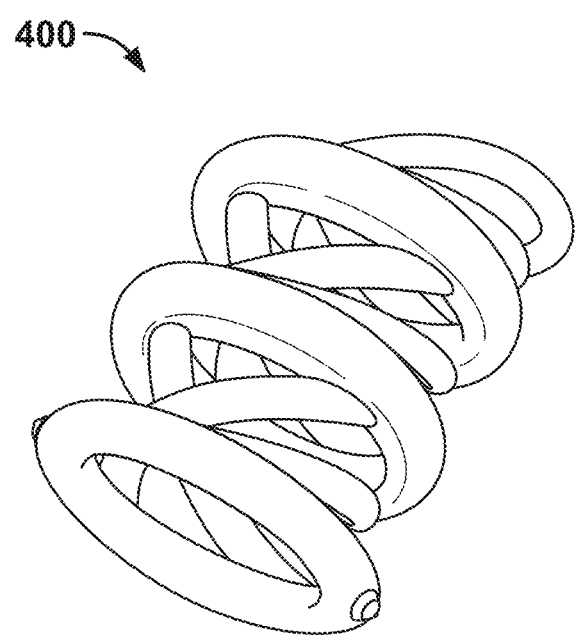
FIG. 6 is a perspective view of a coiled unit cell produced from thermoplastic polymer by 3D printing in accordance with an embodiment of the invention.

A particularly preferred method of 3D printing the unit cells is selective laser melting (SLM). FIG. 6 is an example of a coiled cylindrical unit cell 400 that was prepared by SLM. The coiled unit cell was formed with three helical struts supporting a top ring and a bottom ring with an overall height of 7.5 mm, and the helical struts were angled at 120 degrees from each other with a constant pitch of 0.75 per centimeter. The outer and inner diameters of the top and bottom rings were 10 mm and 8 mm, respectively, and the rings were formed with 2 mm round cross-sections. The coiled cylindrical unit cells formed by 3D printing may be assembled into lattices by fusing the unit cells together. The unit cells may be fused, for example, by application of heat, pressure and or solvent.

Figure 7:
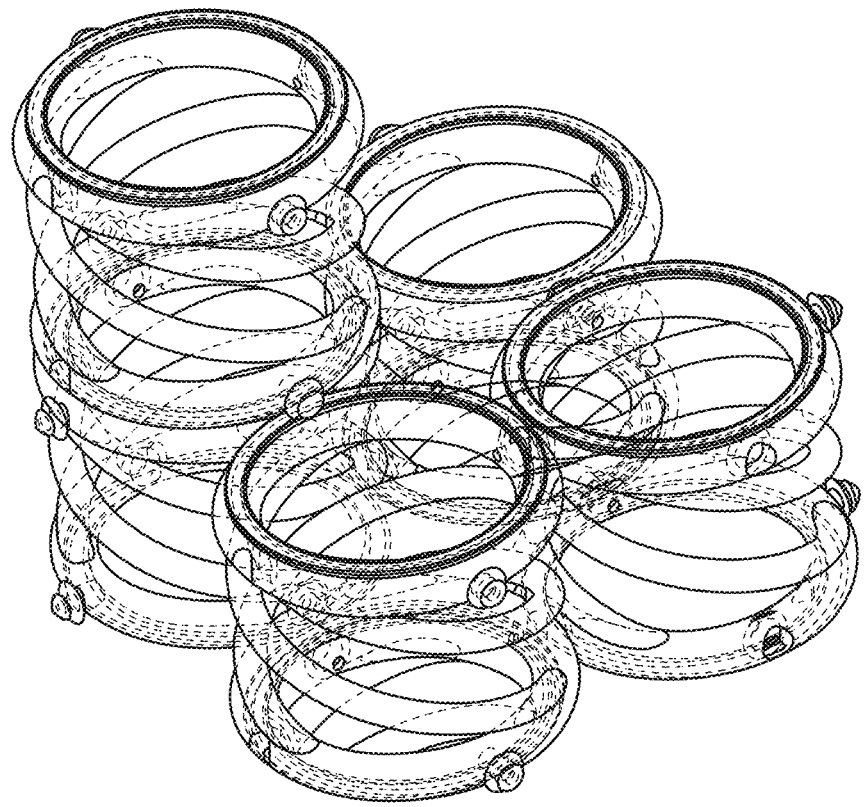
FIG. 7 is a perspective view of a lattice structure of an implant formed from the multiple coiled unit cells shown in FIG. 5 in accordance with an embodiment of the invention.

3D Printing can also be used to form coiled cylindrical unit cells with built-in fasteners as illustrated in the example in FIG. 5. After printing, the coiled cylindrical unit cells comprising fasteners 66, 68 (as illustrated in FIG. 5) can be assembled together by connecting the male and female connectors on the top and bottom rings of the unit cells to form a lattice structure 410 of an implant as illustrated in FIG. 7. In a preferred embodiment, the coiled cylindrical unit cells comprising fasteners are assembled into a lattice, wherein the lattice is compressible and regains its original shape after compression. In an even more preferred embodiment, the coiled cylindrical unit cells comprising fasteners are assembled into the lattice of a breast implant, wherein the lattice is compressible and optionally regains its original shape after compression.

Figure 8:
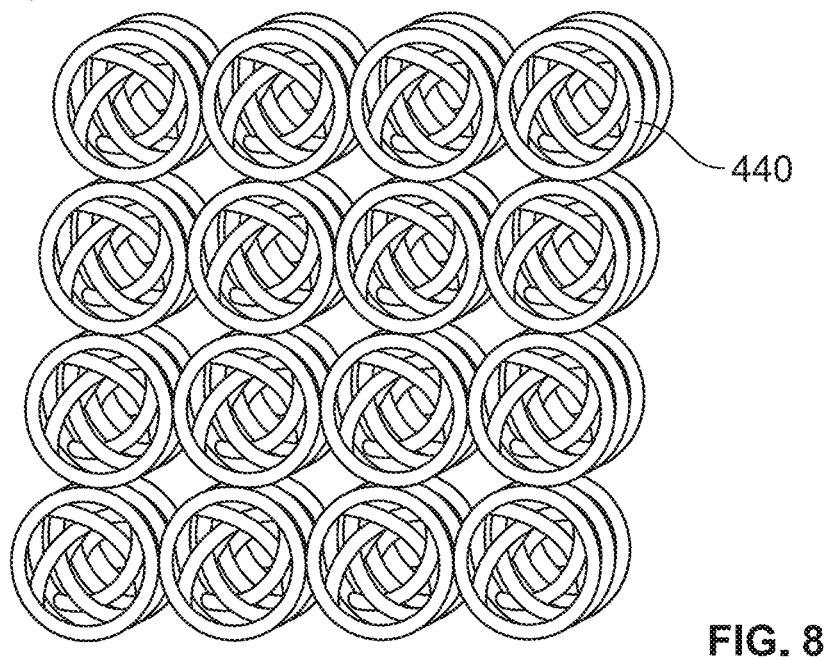
FIG. 8 is an upper perspective view of a lattice structure of an implant formed by 3D printing the multiple coiled cylindrical unit cells illustrated in FIG. 4 to form the lattice structure of the implant in accordance with an embodiment of the invention.

3D Printing can also be used to directly form the lattice structure of the implant without the need to assemble the lattice from individual unit cells. FIG. 8 is a picture of a lattice structure 430 of an implant formed by 3D printing multiple coiled cylindrical unit cells 440, similar to those illustrated in FIG. 4, wherein the unit cells are connected to one another during printing of the lattice. In a preferred embodiment, the lattice so formed is compressible and regains its original shape after compression. In an even more preferred embodiment, the 3D printed lattice is a lattice of a breast implant, wherein the lattice is compressible and regains its original shape after compression.

In other preferred embodiments, lattices with skeleton polyhedron unit cells may be formed directly by 3D printing. An example of a 3D printed implant lattice 10 made from skeleton polyhedron unit cells is shown in FIG. 1. In a preferred embodiment, the 3D printed lattice of the implant is compressible as shown in FIG. 3, and can regain its original shape after compression. In a particularly preferred embodiment, a lattice of a breast implant is formed by 3D printing a lattice of skeleton polyhedra wherein the lattice is compressible. Even more preferably, the lattice regains its original shape after compression. In embodiments, the 3D printed lattices, including 3D printed lattices of breast implants, comprise skeleton polyhedron unit cells wherein the shapes of the unit cells are: tetrahedron, cuboid, pentahedron, hexahedron, heptahedron, octahedron, icosahedron, decahedron, dodecahedron, tetradecahedron, and prisms, antiprisms, and truncated polyhedra thereof. In a preferred embodiment, these skeletal unit cells have 4, 6, 8, 12 or 20 faces. In another embodiment, these skeletal unit cells are formed from elongated polyhedra. In a particularly preferred embodiment, the skeletal unit cells of the 3D printed implants, including breast, nipple, face or buttock implants, are dodecahedrons, even more preferably rhombic dodecahedrons. In other embodiments, the lattice may be 3D printed from two or more different types of skeletal unit cells. For example, the lattice may be printed from a combination of dodecahedron and octagonal shapes.

In other embodiments, the unit cells of the lattices may be prepared by injection molding. For example the unit cells 40, 60 shown in FIGS. 4 and 5, respectively, may be prepared by injection molding, and the unit cells assembled to form lattices. Injection molded unit cells 40 of the type shown in FIG. 4 may be formed into lattices by fusing the unit cells together, for example, using heat, pressure and or solvent. Injection molded unit cells 60 of the type shown in FIG. 5 may be formed into lattices by connecting the male and female connectors. In a preferred embodiment, the injection molded unit cells are formed into lattices that are compressible, and optionally regain their original shape after compression. In a particularly preferred embodiment, the injection molded unit cells are formed into lattices of breast, nipple, face and buttock implants, that are compressible. Preferably, these lattices regain their shape after compression.

The mesh unit cells may be prepared by preparing two meshes are connecting them with struts or fibers to form unit cells. In a preferred embodiment, the mesh unit cells are prepared using a double needle bed knitter. With reference to FIGS. 12-15, a top plate 110 of the mesh unit cell 100 may be knitted on the front bed of a double needle bed knitter, and the bottom plate 120 of the mesh unit cell 100 may be knitted on the back bed of the double needle bed knitter. Fiber, preferably monofilament fiber, may be interlaced between the front and back beds to form the mesh unit cell. Preferably, the mesh in the mesh unit cells is a warp knit, and may be prepared using the double needle bed knitter. In a particularly preferred embodiment, the mesh unit cell comprises warp knit mesh on opposite sides of the unit cell that is interlaced with monofilament fiber to form the mesh unit cell. In a particularly preferred embodiment, the mesh unit cells comprise warp knit meshes interlaced with monofilament fiber and are compressible.

In a preferred embodiment, the mesh unit cells are prepared from fibers, preferably monofilament fibers, with one or more of the following polymers or copolymers: poly-4-hydroxybutyrate and copolymer, and poly(butylene succinate) or copolymer. These polymers and copolymers may further comprise one or more of the following: branching agents, cross-linking agents, chain extender agents, and reactive blending agents. Particularly preferred implants made from mesh unit cells using these polymer compositions may be used as breast implants.

The mesh unit cells may be assembled into implants using any suitable method. For example, the mesh unit cells may be formed into the lattices of implants by fusion. For example, by the application of heat, pressure and or solvent. More preferably, the mesh unit cells may be connected together using fiber. In an embodiment, the mesh unit cells may be sewn together using fiber.

In an embodiment, the unit cells are made of foam and the foam unit cells may be assembled into implants. For example, the foam unit cells may be formed into lattices of the implant by fusion. For example, by the application of heat, pressure and or solvent. More preferably, the lattices of the implants comprising foam unit cells may be formed from foam unit cells comprising male and female anchors by connecting the male and female anchors together.

D. Physical Properties of the Implant's Lattice

In an embodiment, the mechanical properties of the lattice are designed so that they approximate the mechanical properties of tissue. In one embodiment, the elastic modulus of the lattice of the implant is between 0.01 kPa to 290 MPa, more preferably from 0.1 kPa to 10 MPa, and even more preferably from 0.1 kPa to 1 MPa or 0.1 kPa to 100 kPa. In a particularly preferred embodiment, the implant is a breast implant, and the lattice of the breast implant has an elastic modulus that is 0.01 kPa to 1 MPa, and more preferably 0.01 kPa to 100 kPa. In another embodiment, the implant is a breast implant, and the lattice of the breast implant has an elastic modulus that is ±50% of the elastic modulus of breast tissue. In other embodiments, the lattice of the implant has an elastic modulus that is ±50%, more preferably ±25% of the elastic modulus of glandular tissue, adipose tissue, skin, pectoralis fascia, or breast tissue. For reference, the elastic modulus values of glandular tissue, adipose tissue, skin, pectoralis fascia, and breast tissue have been reported to be 7.5-66 kPa, 0.5-25 kPa, 200-3,000 kPa, 100-2,000 kPa, and 0.167-29 kPa respectively. In a particularly preferred embodiment, the lattice of a breast implant comprising the skeleton polyhedron unit cells, spiral or coiled unit cells, or mesh unit cells has an elastic modulus that is 0.167 kPa±50% to 66 kPa±50%.

Figure 10A:
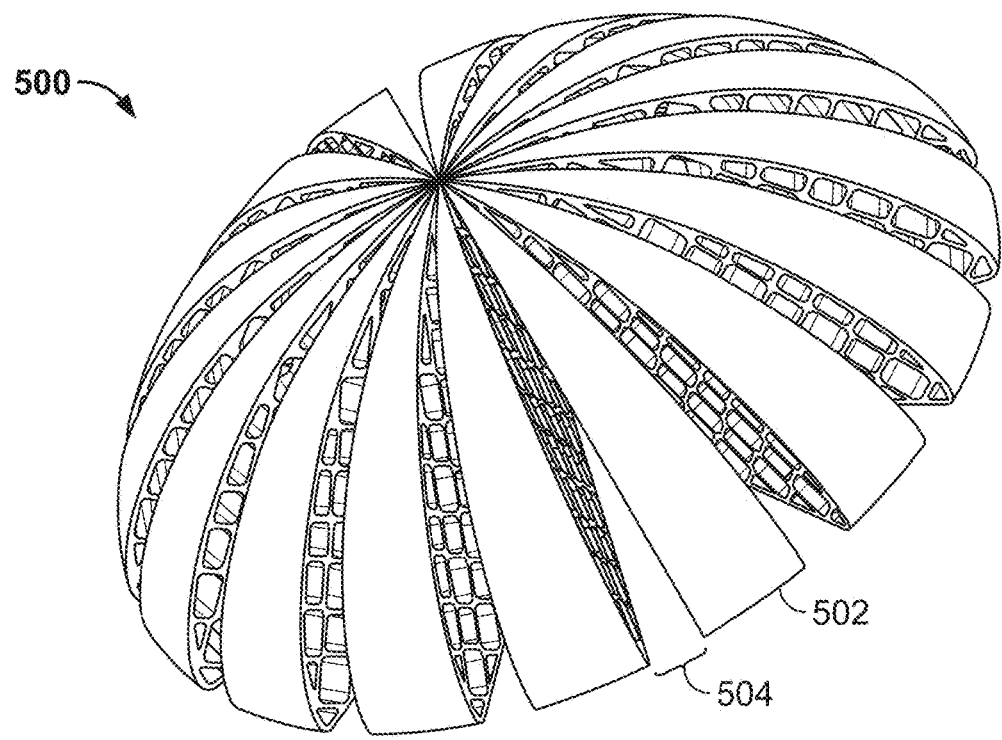
FIG. 10A is an upper perspective view of another breast implant comprising skeletal polyhedron unit cells in accordance with an embodiment of the invention.
Figure 10B:
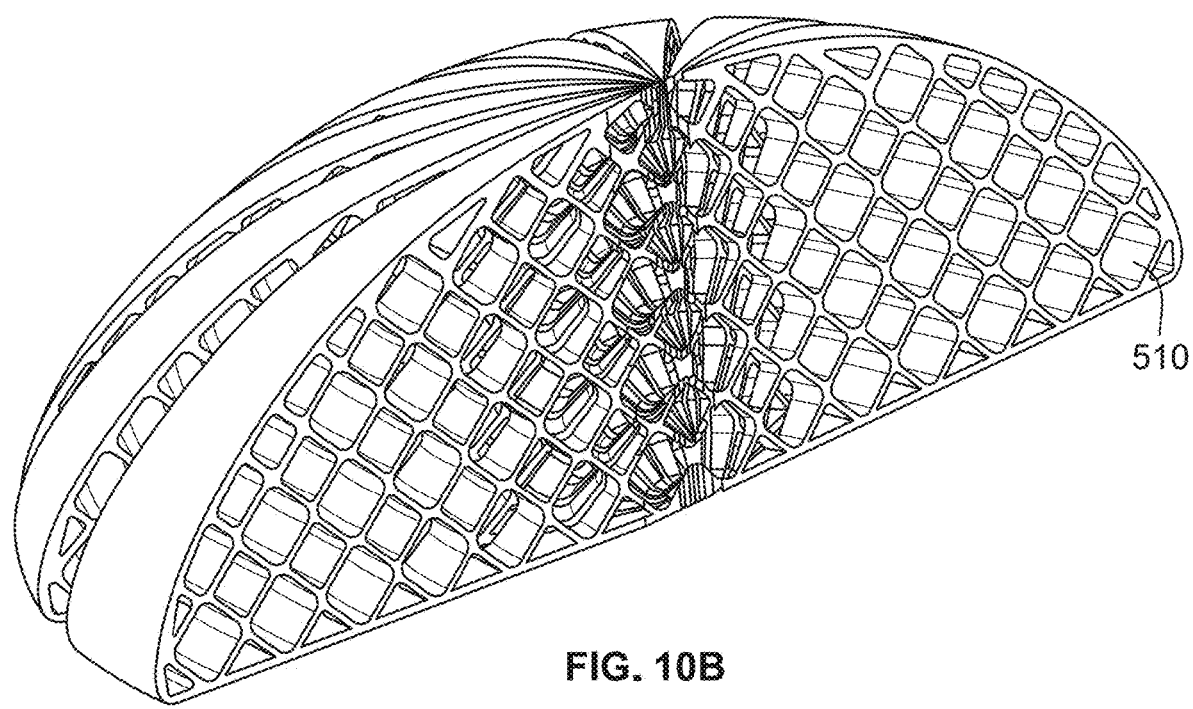
FIG. 10B is cross-section of the implant shown in FIG. 10A showing the skeletal polyhedron unit cells of the implant.

FIG. 10A shows an example of a breast implant 500 with a spring design that provides the implant with a compressive modulus similar to breast tissue. Implant 500 includes segments 502, defining a gap 504 between adjacent segments. A cross-section of the breast implant is shown in FIG. 10B. In this example, the lattice of the implant is made from stacked diamond unit cells 510. The implant has a large surface area that can be coated, for example, with autologous fat, cells, collagen or bioactive agents.

Figure 11:
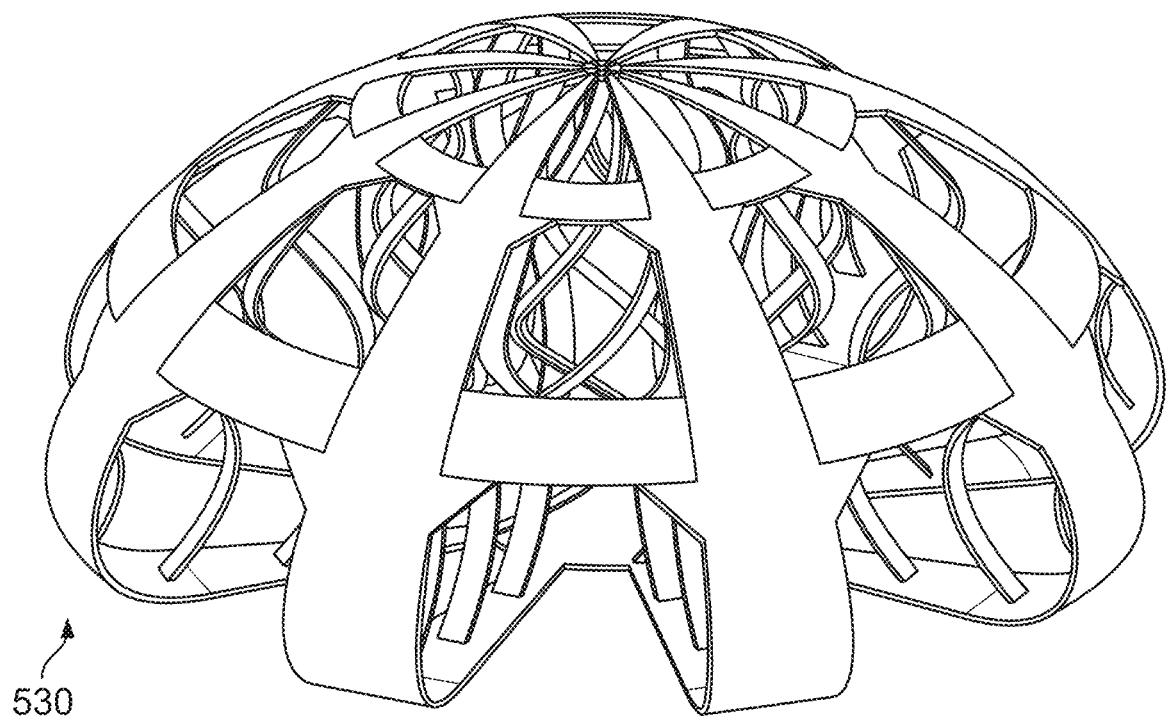
FIG. 11 is an upper perspective view of another implant in accordance with an embodiment of the invention.

FIG. 11 is a picture showing an alternative embodiment of a breast implant 530 designed to have an elastic modulus similar to breast tissue.

In another embodiment, the lattice of the implant may have anisotropic properties. That is, the lattice may have different properties in different directions. For example, the lattice may have a first elastic modulus in one direction, and a second different elastic modulus in a second direction. In an embodiment, the implant may be a breast implant, and the lattice of the breast implant may have a first elastic modulus in one direction, and a second different elastic modulus in a second direction. The lattices of the breast implants may have different properties in the superior to inferior directions of the breast versus the properties in the lateral to medial directions of the breast. In one embodiment, the unit cells of the lattice may be elongated in one direction in order to provide a lattice with anisotropic properties. For example, the unit cells of the lattice may be elongated in a first direction in order to provide a lattice with an increased elastic modulus in that first direction.

In order to allow tissue in-growth into the lattice of the implant, the lattice should have a strength retention long enough to permit cells and blood vessels to invade the implant and proliferate. In embodiments, the lattice of the implant has a strength retention of at least 25% at 2 weeks, more preferably at least 50% at 2 weeks, and even more preferably at least 50% at 4 weeks. In other embodiments, the lattice of the implant is designed to support mechanical forces acting on the implant, and to allow a steady transition of mechanical forces from the lattice to regenerated host tissues. In particular, the lattice of a breast implant is designed to support mechanical forces acting on the breast implant, and to allow a steady transition of mechanical forces from the lattice to new host tissues.

E. Other Features of the Implants

The implants or lattices of the implants may be trimmed or cut with scissors, blades, other sharp cutting instruments, or thermal knives in order to provide the desired implants or lattice shapes. The implants or lattices can also be cut into the desired shapes using laser-cutting techniques. This can be particularly advantageous in shaping fiber-based, mesh-based and strut-based implants because the technique is versatile, and importantly can provide shaped implants and lattices without sharp edges.

In embodiments, the implants may further comprise pillars to reinforce the implants or to facilitate implantation. The pillars may, for example, help to reshape the implant following implantation. Preferably, the pillars are incorporated into the lattice structures in order to reinforce the implants or facilitate implantation of the implant. The pillars may be incorporated into the implants by any suitable method, including fusion, molding, weaving, knitting, or printing. In a preferred embodiment, pillars are incorporated by fusing absorbable polymeric fibers or struts to the lattice of the implant. In embodiments, the pillar may have diameters or widths ranging from 0.1 to 5 mm, and more preferably 0.5 to 3 mm. The absorbable polymeric fibers or struts may be oriented or unoriented, but are preferably unoriented, and more preferably unoriented poly-4-hydroxybutyrate fibers or struts. In another embodiment, flexible pillars may be printed directly onto the lattice of the implant, or incorporated into the lattice during printing of the lattice.

The implants may comprise retainers, such as barbs or tacks, so that the implant can be anchored in the body without the use of sutures. The implants preferably contain the retainers in the outlying borders of the implant or lattice structure of the implant. When the implant is a breast implant, the retainers are preferably located on the implant to allow the implant to be anchored to the chest wall.

The implant may comprise suture tabs so that the implants can be anchored in the body using for example sutures and or staples. The number of tabs may vary. In one embodiment, the number of tabs will depend upon the load exerted on the implant. A larger number of tabs may be desirable when the implant is heavier or more bulky. In embodiments, the implant comprises 1, 2, 3, 4, 5, 6, 7, 8, 9, 10, 11, 12, 13, 14, 15, 16, 17, 18, 19, 20 tabs or more, but preferably 4-12. When the implant is a breast implant, the implant preferably contains 4 or more tabs, preferably 4-12 tabs, in order to anchor the breast implant to the chest wall. The dimensions of the tabs are preferably from 0.5 cm×0.5 cm to 5 cm×4 cm, preferably 2 cm×2.5 cm. The tabs attached to the implant must have sufficient strength retention in vivo to resist mechanical loads, and to allow sufficient in-growth of tissue into the implant in order to prevent subsequent movement of the implant after implantation. In a preferred embodiment, the suture pullout strength of the tabs attached to the implant, is greater than 10 N, and more preferably greater than 20 N.

F. Implant Coatings and Fillings

In embodiments, the implants are fabricated with coatings and or some or all of the lattice is used as a carrier. For example, the lattice may be fabricated by populating some or all of the void space of the lattice with cells or tissue, including autograft, allograft or xenograft tissue and cells, and vascularized pedicle. Examples of cells that can be inserted into the void spaces of the implant, and coated on its surfaces, include adipose cells, fibroblast cells, and stem cells. In a preferred embodiment, autologous fat, fat lipoaspirate, or injectable fat, is coated on the implant and inserted into void space of the implant. In another preferred embodiment, a vascularized pedicle may be inserted into void space of the implant. In yet another preferred embodiment, the implant can be coated or partially or fully filled with one or more bioactive agents. Particularly preferred bioactive agents that can be coated on the implant or used to partially or completely fill the implant include collagen and hyaluronic acid. In other embodiments, the implant may be coated with one or more antibiotics.

Any suitable method can be used to coat the implant and fill its void space with cells, tissue, bioactive agents and other additives. In embodiments, the implant is filled or coated with cells, tissue, bioactive agents and other additives by injection, spraying, or dip-coating. Collagen may be applied to the implant by coating and freeze-drying. In a particularly preferred embodiment, the implants may be coated or partially or completely filled with cells, tissue, bioactive agents and or other additives by injection using needles that can be inserted into the lattice of the implant without damaging the lattice. In one embodiment, the needles used for injection of cells, tissue, fat, fat lipoaspirate, bioactive agents, collagen, hyaluronic acid, and other additives have outer diameters between 0.5 mm and 5 mm.

IV. Methods for Implanting the Implants

In embodiments, the implant is implanted into the body. Preferably, the implant is implanted into a site of reconstruction, remodeling, repair, and or regeneration. In a preferred embodiment, connective tissue and or vasculature will invade the lattice of the implant after implantation. In a particularly preferred embodiment, the implant comprises absorbable materials, and connective tissue and or vasculature will also invade the spaces where the absorbable materials have degraded. The unit cells of the lattices may be colonized by cells prior to implantation or, more preferably, following implantation, and the pores of the lattices invaded by tissue, blood vessels or a combination thereof.

The implants may be coated or filled with transplantation cells, stem cells, fibroblast cells, adipose cells, and or tissues prior to implantation, or after implantation. In embodiments, the implant is coated or filled with differentiated cells prior to, or subsequent to, implantation. Differentiated cells have a specific form and function. Examples include fat cells and muscle cells. Preferably the implants are populated with cells by injection, before or after implantation, and more preferably by using needles that do not damage the lattice of the implant. The implants may also be coated or filled with platelets, extracellular adipose matrix proteins, gels, hydrogels, and bioactive agents prior to implantation. In an embodiment, the implant may be coated with antibiotic prior to implantation, for example, by dipping the implant in a solution of antibiotic.

The implants may be used to deliver autologous cells and tissue to the patient in a specific location, such as the breast, nipple, face and buttock. The autologous tissue is preferably one or more of the following: autologous fat, fat lipoaspirate, injectable fat, adipose cells, fibroblast cells, and stem cells.

The implants may be used for lipofilling and delivering fat tissue into a patient. In a particularly preferred embodiment, autologous fatty tissue is prepared prior to, or following, implantation of the implant, and is injected or otherwise inserted into or coated on the implant prior to or following implantation of the implant. The autologous fatty tissue is preferably prepared by liposuction at a donor site on the patient's body. After centrifugation, the lipid phase containing adipocytes is then separated from blood elements, and combined with the implant prior to implantation, or injected, or otherwise inserted into the implant following implantation. In an embodiment, the implant is injected with, or filled with, a volume of lipoaspirate that represents 1% to 50% of the total volume of the lattice, and more preferably 1% to 20% of the total volume of the lattice.

In another embodiment, lipoaspirate fatty tissue taken from the patient may be mixed with a biological or synthetic scaffold matrix, such as very small fibers or particles, prior to adding the lipoaspirate to the implant. In this embodiment, the added matrix serves to hold or bind micro-globules of fat, and disperse and retain them within the lattice of the implant. In some embodiments, the use of added matrix can help to prevent pooling of fat which could lead to necrosis, and or help to increase vascularization of the implant.

In another embodiment, a vascular pedicle or other tissue mass is harvested from the patient, and inserted into the implant. The pedicle or other tissue mass may be inserted into the implant prior to implantation of the implant, and then the implant with the pedicle or other tissue mass implanted in the patient, or the pedicle or other tissue mass may be inserted into the implant after the implant has been implanted in the patient.

In a preferred embodiment, the implant is implanted into the breast of a patient. In a further embodiment, an implant is implanted and fixated in both breasts. In embodiments, the implants are implanted in patients during mastopexy and augmentation procedures, including revision procedures. In a particularly preferred embodiment, the implant is implanted in a patient that has undergone a: (i) mastectomy, (ii) breast lift and has need of augmentation, (iii) breast reduction and needs support, lift or remodeling of the reduced breast, or (iv) previous silicone or saline breast implant surgery and desires the silicone or saline implant to be removed and that a subsequent reconstruction of the breast will provide a fuller or large sized breast. The implant may also be implanted in a breast surgery patient to increase the projection of the breast away from the chest, and optionally additional fat graft volume added to the implant after implantation to increase the projection. Additional fat graft volume may be added to the implant immediately after implantation of the implant, but may also be added at follow up visits. For example, additional fat graft volume may be added to the implant on one or more occasions that are days, weeks, or months following the implantation of the implant. The procedures described herein can also be performed with removal of breast tissue, resection and redistribution of breast tissue.

In an embodiment, a method of implantation of the implant in the breast comprises at least the steps of: (i) making at least one incision to gain access to the breast tissue of the patient, (ii) separating the skin and subcutaneous fascia from the breast mound of the breast, (iii) positioning the implant on the breast mound of the breast, (iv) securing the implant to the tissue surrounding the breast mound of the breast, and (v) closing the incisions in the breast. Preferably, this method further comprises one or more of the following steps: (a) preparing a sample of lipoaspirate, and coating or filling the implant with the sample prior to implantation of the implant, (b) preparing a sample of lipoaspirate, and coating or filling the implant with the sample after implantation of the implant, preferably by injecting the sample into the implant, (c) inserting a vascular pedicle into the implant prior to, or after, implantation of the implant, and (d) suturing or stapling the implant in place. In a preferred embodiment, the implant is implanted in a sub-glandular, sub-pectoral or pre-pectoral position. In embodiments, the implant is sutured to the tissue surrounding the breast mound, and even more preferably to the fascia surrounding the pectoral muscle underlying the breast mound. In another embodiment, the implant comprises tabs, and the tabs are sutured to the tissue surrounding the breast mound.

The implant may also be coated or filled with cells and tissues other than fat grafts prior to, or subsequent to, implantation, as well as with cytokines, platelets and extracellular adipose matrix proteins. For example, the implant may be coated or filled with cartilage or dermal grafts. The implants may also be coated or filled with other tissue cells, such as pancreatic islet cells, hepatic cells, or stem cells genetically altered to contain genes for treatment of patient illnesses.

In embodiments, the implant is implanted into the body. Preferably, the implant is implanted into a site of reconstruction, remodeling, repair, and or regeneration. In a preferred embodiment, connective tissue and or vasculature will invade the lattice of the implant after implantation.

In an embodiment, the implant has properties that allows it to be delivered by minimally invasive means through a small incision. The implant may, for example, be designed so that it can be rolled or folded to allow delivery through a small incision. This minimally invasive approach can reduce patient morbidity, scarring and the chance of infection. In an even more preferred embodiment, the implant has a three-dimensional shape and shape memory properties that allow it to assume its original three-dimensional shape unaided after it has been delivered through an incision and into an appropriately sized dissected tissue plane. For example, the implant may be temporarily deformed by rolling it up into a small diameter cylindrical shape, delivered using an inserter, and then allowed to resume its original three-dimensional shape unaided in vivo.

EXAMPLES

The present invention with be further understood by reference to the following non-limiting example.

Example 1: Implant with Porous Lattice of Connected Skeletal Polyhedron Unit Cells Formed by SLS Printing The implant shown in FIG. 1 was prepared as described herein. Pellets of P4HB (Tepha, Inc., Mw 480 kDa) were subjected to cryo-milling followed by sequential sieving to yield P4HB powder with a particle size ranging from 40 to 60 microns. The P4HB powder was produced from P4HB pellets with an average size of 2 mm×2 mm×3 mm that were cooled down to −70° C. and injected with high speed crossing collision paths in a cryo-mill. The resulting powder was sieved using a 60 micron sieving shaker followed by a 40-micron sieving shaker to truncate particles larger than 60 microns and smaller than 40 microns. Sieved P4HB powder (40-60 micron particles) was then dried, flushed with nitrogen, and foil packaged. The P4HB powder had a moisture content of less than 650 ppm. The P4HB powder was loaded in the powder bed of a 3D selective laser sintering (SLS) printer. The thickness of the powder layer was set to 100 micron, laser power was set to 0.3 Watts, and the speed of the laser beam was set to 20 cm/s. Under these conditions, the energy per unit area used was 1 J/cm$^2$. The 3D printer was loaded with an STL file to print the open porous scaffold structure of the implant shown in FIG. 1.

The resulting structure had a dome or spherical-cap type shape with a base diameter of 12 cm, and a projection of 5.5 cm (height from base to apex). The implant was formed with a completely interconnected porous architecture with open porosity. The open porosity design of the implant provides a morphology that allows cells to invade the scaffold and proliferate post-implantation. The diameter of the struts of the skeletal unit cells was 1.5 mm, and the distance between the nodes or cross points (i.e. the length (L) of the struts in a unit cell) was 10 mm. The implant had an elastic modulus value of 16 kPa, shape memory, and was compressible as shown in FIG. 3 by light finger pressure.

We claim:
1. A breast implant comprising a porous lattice, wherein the lattice further comprises a plurality of segments defining a plurality of gaps between adjacent segments of the plurality of segments, each of the plurality of segments comprising connected unit cells, and wherein the unit cells are skeletal polyhedrons with the edges and vertices of the skeletal polyhedrons defined by polymeric struts and/or fibers, wherein the skeletal polyhedron unit cells are compressible.

2. The implant of claim 1, wherein a length of the struts or fibers are from 3 mm, to 8 mm.

3. The implant of claim 1, wherein each type of unit cell in the lattice is the same.

4. The implant of claim 1, wherein the struts or fibers have a thickness or diameter from 50 μm to 5 mm.

5. The implant of claim 1, wherein the porous lattice comprises a plurality of pores, and the pores of the lattice have a diameter of at least 0.5 mm.

6. The implant of claim 1, wherein the elastic modulus of the lattice is between 0.01 kPa and 1 MPa such that the implants can recover their shape after being compressed.

7. The implant of claim 1, wherein the struts and/or fibers have one or more of the following properties: (i) breaking load of 0.1 to 200 N; (ii) elongation at break of 22% to 1,000% ; and (iii) elastic modulus of 0.05 to 10 GPa.

8. The implant of claim 1, wherein the lattice is resorbable.

9. The implant of claim 1, wherein the polymeric struts and/or fibers are made from a polymer or copolymer comprising one or more of the following monomers: 4-hydroxybutyric acid, 3-hydroxybutyric acid, glycolic acid, lactic acid, 1,4-dioxanone, trimethylene carbonate, ε-caprolactone, succinic acid, adipic acid, 1,4-butanediol, and glycol, or comprise poly-4-hydroxybutyrate or copolymer thereof, or poly(butylene succinate) or copolymer thereof.

10. The implant of claim 9, wherein the polymer or copolymer has been cross-linked.

11. The implant of claim 1, further comprising (i) one or more of the following: autologous fat, fat lipoaspirate, injectable fat, adipose cells, fibroblast cells, stem cells, gels, hydrogels, hyaluronic acid, collagen, antimicrobial, antibiotic, bioactive agent, and diagnostic device; (ii) one or more anchors, fasteners or tabs, to fixate the implant; or (iii) one or more openings for insertion of a vascular pedicle, or other tissue mass.

12. The implant of claim 1, wherein the implant is manufactured by a process selected from the group consisting of: (i) forming the struts and/or fibers of the unit cells by injection molding a polymeric composition, and assembling the unit cells to form the lattice of the implant, (ii) forming the lattice of the implant by 3D printing the struts and/or fibers of the unit cells, (iii) forming the lattice of the implant by melt extrusion deposition printing.

13. The implant of claim 1, wherein the porous lattice has a dome-like shape.

14. The implant of claim 1, wherein the edges comprise at least:
a first plurality of edges extending along a first direction;
a second plurality of edges extending along a second direction, the second direction different from the first direction; and a third plurality of edges extending along a third direction, the third direction different from both the first and second directions.

15. The implant of claim 1, wherein at least three edges are directly connected to one another.

16. A breast implant comprising a porous lattice, wherein the lattice further comprises a plurality of segments defining a plurality of gaps between adjacent segments of the plurality of segments, each of the plurality of segments comprising connected unit cells, and wherein the unit cells are skeletal polyhedrons with edges and vertices of the skeletal polyhedrons defined by polymeric struts and/or fibers, wherein the skeletal polyhedron unit cells are compressible, and wherein the edges comprise at least:
   a plurality of edges;
   a second plurality of edges directly connected to the first plurality of edges; and a third plurality of edges directly connected to the first plurality of edges and to the second plurality of edges.

17. The implant of claim 16, wherein each unit cell in the lattice is the same.

18. The implant of claim 16, wherein the struts or fibers have a thickness or diameter from 50 μm to 5 mm.

19. The implant of claim 16, wherin the porous lattice comprises a plurality of pores, and the pores of the lattice have a diameter of at least 0.5 mm.

20. The implant of claim 16, wherein the elastic modulus of the lattice is between 0.01 kPa and 1 MPa such that the immplants can recover their shape after being compressed.

21. The implant of claim 16, wherein the lattice is resorable.

22. A method of implanting an implant as recited in claim 1 in the breast comprising: (i) making at least one incision to gain access to the breast tissue of the patient, (ii) separating the skin and subcutaneous fascia from the breast mound of the breast, (iii) positioning the implant pre-pectoral, sub-glandular or sub-pectoral, (iv) securing the implant to nearby tissue, and (v) closing the incisions in the breast.

23. The method of claim 22 further comprising coating or injecting into the implant one or more of the following on one or more occasions either prior to implanting the implant in the patient or after implanting the implant in the patient: autologous fat, fat lipoaspirate, injectable fat, adipose cells, fibroblast cells, stem cells, gel, hydrogel, hyaluronic acid, collagen, antimicrobial, antibiotic, and a bioactive agent.

24. The method of claim 22, wherein the implant is secured to pectoralis fascia.

* * * * *

UNITED STATES PATENT AND TRADEMARK OFFICE
CERTIFICATE OF CORRECTION

PATENT NO. : 11,903,815 B2
APPLICATION NO. : 16/859831
DATED : February 20, 2024
INVENTOR(S) : Skander Limem et al.

Page 1 of 1

It is certified that error appears in the above-identified patent and that said Letters Patent is hereby corrected as shown below:

In the Claims

At Column 34, Claim 2, Line 16 "3 mm, to 8 mm" should read --3 mm to 8 mm--

At Column 34, Claim 3, Line 17 "each type of unit cell" should read --each unit cell--

At Column 34, Claim 12, Lines 53-54 "selected from the group consisting of" should read --selected from one or more of--

At Column 34, Claim 12, Line 58 "(iii) forming the lattice" should read --and (iii) forming the lattice--

At Column 35, Claim 16, Line 15 "a plurality of edges;" should read --a first plurality of edges;--

At Column 35, Claim 19, Line 24 the word "wherin" should read --wherein--

At Column 36, Claim 20, Line 3 the word "immplants" should read --implants--

At Column 36, Claim 21, Line 5 the word "resorable" should read --resorbable--

Signed and Sealed this
Twenty-seventh Day of August, 2024

Katherine Kelly Vidal
*Director of the United States Patent and Trademark Office*